US006436639B1

(12) United States Patent
Kiefer et al.

(10) Patent No.: US 6,436,639 B1
(45) Date of Patent: Aug. 20, 2002

(54) BAK PROMOTER EXPRESSION SYSTEM

(75) Inventors: Michael C. Kiefer, Clayton; Natalya K. Ossina, Albany, both of CA (US)

(73) Assignee: Tanox, Inc., Houston, TX (US)

( * ) Notice: Subject to any disclaimer, the term of this patent is extended or adjusted under 35 U.S.C. 154(b) by 0 days.

(21) Appl. No.: 09/367,750

(22) PCT Filed: Feb. 17, 1998

(86) PCT No.: PCT/US98/02845

§ 371 (c)(1),
(2), (4) Date: Dec. 7, 1999

(87) PCT Pub. No.: WO98/35659

PCT Pub. Date: Aug. 20, 1998

Related U.S. Application Data

(60) Provisional application No. 60/038,412, filed on Feb. 18, 1997.

(51) Int. Cl.[7] .................. C12Q 1/68; C07H 21/04; C12N 1/00; C12N 5/10
(52) U.S. Cl. .................. 435/6; 435/243; 435/325; 435/410; 536/24.1
(58) Field of Search .................. 435/6, 325, 243, 435/410; 536/24.1

(56) References Cited

FOREIGN PATENT DOCUMENTS

| WO | WO95/15084 | * | 6/1995 |
| WO | WO 96/18738 | | 6/1996 |
| WO | WO 98/07879 | | 2/1998 |
| WO | WO 98/35016 | | 8/1998 |
| WO | WO 98/35056 | | 8/1998 |

OTHER PUBLICATIONS

Avraham et al., *J. Biol. Chem.*, 270(46):27742–27751 (1995).

Grimes et al., *Proc. Natl. Acad. Sci. USA*, 93(25):14569–14573 (1996).

Ossina et al., *J. Biol. Chem.*, 272(26):16351–16357 (1997).

* cited by examiner

*Primary Examiner*—Terry McKelvey
(74) *Attorney, Agent, or Firm*—Sheridan Ross P.C.

(57) ABSTRACT

Polynucleotides which regulate the expression of a gene involved in apoptosis is described. Also provided are methods for identifying agents that modulate expression of a gene involved in apoptosis.

20 Claims, 17 Drawing Sheets

```
-4021  gatctgcctg  cctcgggctc  ccaaagtgct  gggatgggat  tacaggcgtg  agccaccgtg  cccggccttt  tttttttttt
-3941  tttttttttt  tctagagaca  gactctccct  ctgttgccct  ggtgcaatca  tagcttactg  cagcctcgac  ctcctggact
-3861  caagcaatcc  tcccacctca  gcctcccag   tagctaagac  cacaggcata  caacaccatg  ccttgctaat  tttttttttt
-3781  tttttttttt  tttttggtat  aagcagggta  ttgctgttgc  ccaggctggc  ctggaactcc  tgcacctggc  ctcaagcgat
-3701  cctcttgcct  tggcctccca  aatggctggg  atgggattct  aggcgtgaca  caccgcagct  ggctgccttt  tttgttgttg
-3621  ttgagacaag  gtcttgctct  gttgcccagg  gcggaatgca  gtggtgcaaa  catggctcac  tgcggcctcg  acttcctgtg
                                               Sp1
-3541  ctcaggtgat  cctcctgcct  cagcctccta  ggtagctggg  accaccaaat  gcacaggtgt  gcactaccat  acccagctaa
-3461  tttctaattt  tttttttgtag  agacatggtc  tcactttgtt  gcccaggctg  gtcttgaact  cctgggctca  agcaatcctc
-3381  ccacctcagc  cttccaaagt  gttgggatta  caggcgtgag  ccactggcc   cagcctctat  tgagttttaa  tctccgttta
-3301  cttgactatc  accttcagga  tttcaaacat  ccagagacca  ccaaggtgca  tggtgcacag  gtctaaattg  caggttgaat
-3221  ctcaatctag  tattagtatt  ccccaatgcg  actacagaac  tgattattac  tatttatttt  ttttttgagat ggagtcttgc
-3141  actgtcacca  gggctggagt  gcaatggcgc  aatcctggtt  tactgcaacc  tccacctccc  aggttcaagg  gattctcctg
                                                                                          NFkB1
-3061  cctcagcctt  ccaactagct  gggattacag  gcgcccgcca  ccacacccag  ctaatttttt  gtattttag   tagagacggg
-2981  gtttcaccat  gttagccaga  atggtctcga  tctcttgacc  tcgtgatctg  cctgcctcag  cctcccaagg  tgctgggatt
       NFkB2
-2901  ataggcgtga  gccaccgcgc  ctgcccaga   actgatgatt  aacccagatg  agcctctgtt  catctgaatg  ggtattgtca
-2821  acagcactca  cttacaagag  ttgctgagaa  gatccaatga  gacaaatagt  tgctaaagtg  ccaggcatgc  agcagtgctt
-2741  aagaaacttc  tcaccctggg  ttttttattg  gtattgattg  atgtagaggt  ggggagaag   atcaaagaca  aggattgaga
-2661  atcagggatg  ggaaaagcag  tgggccactg  acagccgccc  tgcctgcctg  ggaggtgggg  tggggaaagt  gggcgggaca
                                                Sp1                                       Sp1 p53
                                                                                              *
-2581  tgctcctggg  cctggcccac  ccagatcacc  cctacaggct  gtcggcctgt  gcgtctgcat  ccggtggcca  cagaGCAACT  Exon 1
                 p53         p53                           *          *         P2            P1
-2501  TCCTCTAGAG  GGAGCTGATT  GGAGCCGGGT  GCCGCTGGCA  CCTCTATGAT  CACTGGAGTC  TCGCGGGTCC  CTCGGGCTGC
                  P3
-2421  ACAGGGACAA  GTAAAGGCTA  CATCCAGATG  CCGGGAATGC  ACTGACGCCC  ATTCCTGGAA  ACTGGGCTCC  CACTCAGCCC
                       *                                    Sp1        GAS
-2341  CTGGGAGCAG  CAGCCGCCAG  CCCCTCGGGA  CCTCCATCTC  CACCCTGCTG  AGCCACCCGG  GTTGGGCCAG  GATCCGGCA
                                                          PER 14                          Bam H1
-2261  Ggtaagctgg  aagggtcttg  tccatcctcc  cagatctcag  cagcccagc   cccagggtgg  ggcagggagc  ctgccggag
-2181  ccgggtgggg  aaggggaagc  tcaaggcttc  cctgggcagg  tctgccgccc  cggctgggga  cctgatcctg  ccatgcctgc
-2101  ctctggctgc  ccctcacagc  ttcccctctt  ggcccagccc  tggatgccgg  agaactgtaa  gaactgggtc  ctttaacagt
-2021  ctgggagatg  ggagtggagg  tcagagccaa  ggtcaagggc  agagagagaa  ctttctcagc  gcttgctgct  gcccaacatc
-1941  cctagactgg  gtccagggcc  tggccaggca  tgtatccctg  gggaacattc  atcggggccc  agcaagccca  ggaagtcggg
-1861  ggtgctccc   ctcaccggga  atttaggcca  cttggatggg  ggaggcagag  ctaggcctga  gtcagcatag  gttgctggcc
-1781  ttggtgggtg  ttctgaggct  ctacctgctc  ccctcggaag  cctgggtgt   tggtagaggg  agttggaggt  gcagtcagca
-1701  tcctccagcc  tctactgtcct  ggggtgccg   ggtcctggag  actgggaag   aaggaaggcc  atcttatgta  aggagctacg
-1621  gggggtggga  ggcaagcaaa  actcttttt   ttgttttttt  gaaatgggagt ctcgctctgt  tgcccaggct  ggagtgcagt
-1541  ggcgcaatct  cggctgaccg  caacctccgc  ctccaaggtt  caagcgattc  tcctgcctca  gcctcccgag  tagctgggac
-1461  tacaggcgca  cgcaccatgc  ccagctaatt  tttgtattt   tagtagagat  ggggtttcat  tatgttggcc  aggctggtct
-1381  tgaacttctg  acctcgtggg  ccactatgcc  cggctgcaaa  gttctgtttt  aacaaggcct  tgccctaga   ggtggaggag
-1301  aggagggtct  gccttcgccc  tgtccctgtc  cggcagatcg  aggaggagtg  gggagctggg  tgagggcaca  ggtggtccag
-1221  gtccccaggc  cctgggcggt  ggggtgggg   ctgtgtgctt  ggcccagggt  ggggctgcac  acccctccc   tctgggatag
-1141  gaggagggcg  ctctccttct  gagggctgga  ggctgcctgg  ggaaatgggg  ctctgggagg  ggtgcaaact  gaaagtgaaa
                                                                                         ISRE
-1061  cagctgacat  ccaggaaaca  ctcaccctga  tgagggtca   cagcaggttg  gggctgcggt  caggaccagg  ..........
-101   cctgtatggg  gtccccagtc  acaggtctgt  gctcacccccc atctctgctt  tttctcgccc  ttccccgcag  GCTGATCCCG  Exon 2
-21    TCCTCCACTG  AGACCTGAAA  A ATG GCT  TCG GGG CAA  GGC CCA GGT  CCT CCC AGG  CAG GAG TGC GGA ...
                               M   A     S   G   Q    G   P   G    P   P   R    Q   E   C   G  ...
```

```
-1061  cagctgacat ccaggaaaca ctcaccctga tgaggggtca cagcaggttg gggctgcggt caggaccagg caaagaggaa
 -981  aattggggcc ggggacagaa gaccaggtgt gtggtgggag tacgaggcag gttatggggc ttcaaagaag gccctgatcc
 -901  agaacacact ctgaggtcca caaactgaa  aagaaatctt gcatgcgtgt tgagtacatg gactcacgga gattcagaca
 -821  aacaacctga ctttccgtga ctaacgatgt gacctcgggg cactcaactc tttgtgcctc actttcctg  cctgtaaagt
 -741  gggtatgatg gcgctcaccc tgctgggttc atgtgagttt ccagtgttca ccaccacag  agtgctccta agtgggagag
 -661  tatatcttag gctctcagga aatgtttgcg gctaacagcc cagagttaaa aaacaggtgt gttctgcca  gccagaggga
 -581  agtaggcct  ctgaggacag ccttcatggg ccattggctg ggcagtggct cgcttgcaat aagcatgtgc tgggtgggct
 -501  gcaggaggcc ccaggaacag ctaaaaaccc cccaggctct tgcccagga  gtggcatgaa ctgagagcc  agcggcact
 -421  gctgcagcca caccctcctc gatggtgcag atacctcagt ctgccctggg ctgcctcacc ttcttaccct gtctccctca
 -341  aagagggagt gttcagtaag ttgtttccta ccagcagact tcactgggac ccatgctgga gtaagaataa aaagtcccag
 -261  aggaggccag gcacggtggc tcacacctgt aatcccagca ctgtggatgg ccgaggcaga ctcacgaggt caggagtttg
 -181  agaccggcct ggccaaagtc ccagaggact aagggccttt ctgggaatgg gggatcctct ctcctatgtg gacatggcaa
 -101  cctgtatggg gtccccagtc acaggtctgt gctcacccc  atctctgctt tttctcgccc ttccccgcag GCTGATCCCG  Exon 2
  -21  TCCTCCACTG AGACCTGAAA A ATG GCT TCG GGG CAA GGC CCA GGT CCT CCC AGG CAG GAG TGC GGA ...
                             M   A   S   G   Q   G   P   G   P   P   R   Q   E   C   G   ...
```

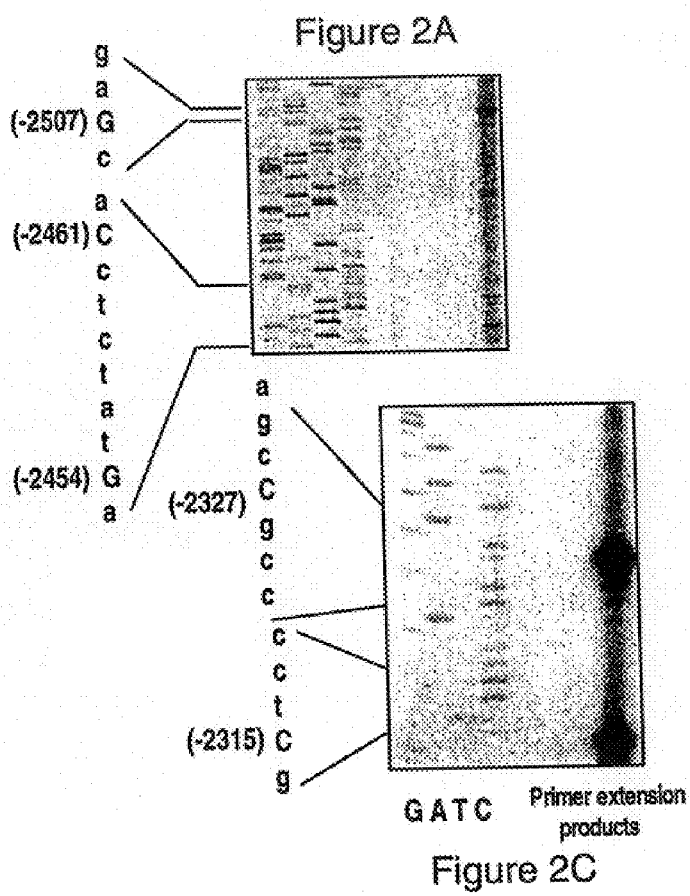

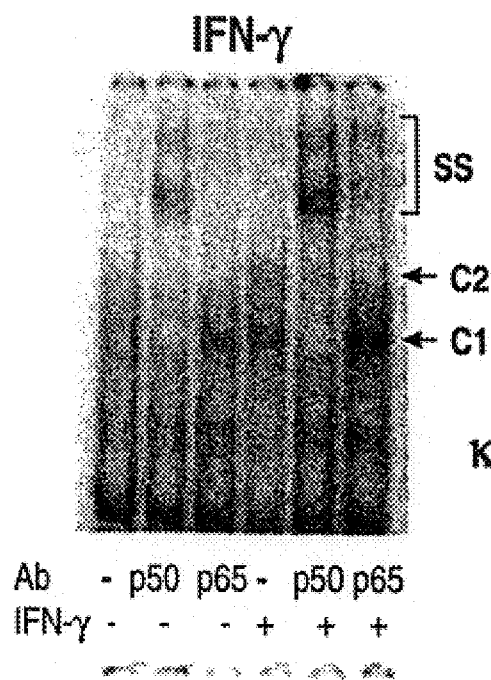
Figure 7A
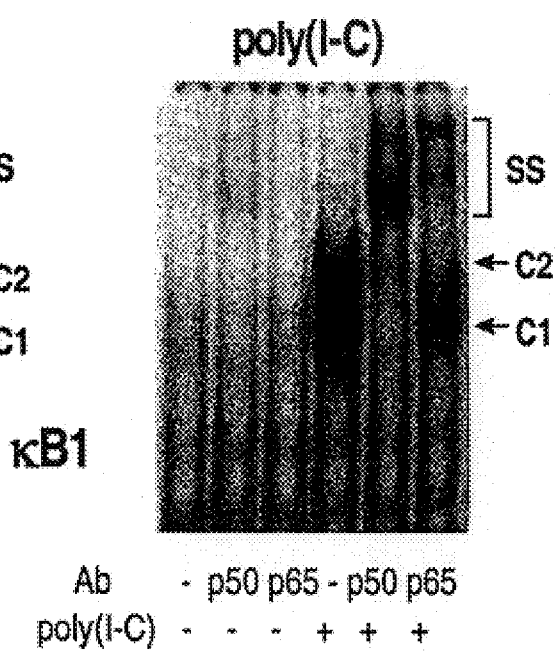
Figure 7B
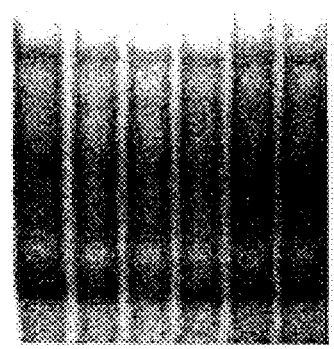

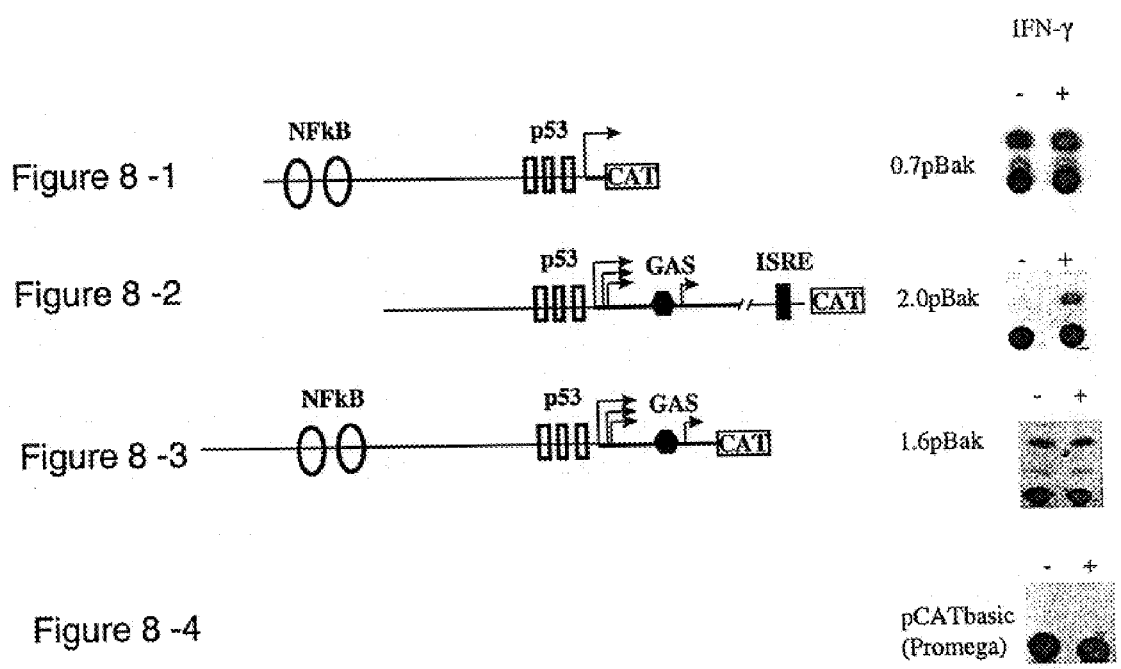

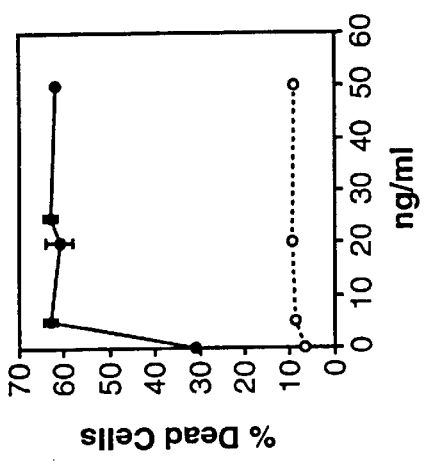
Figure 9A(1) Anti-Fas
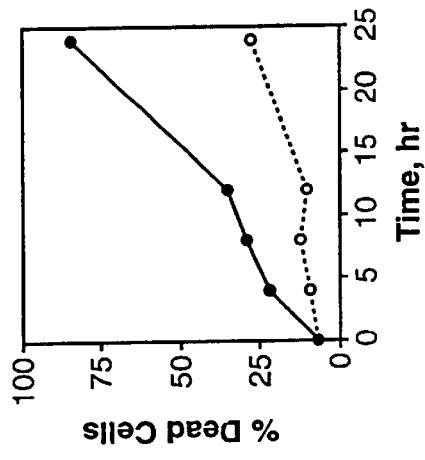
Figure 9B(1) TNF
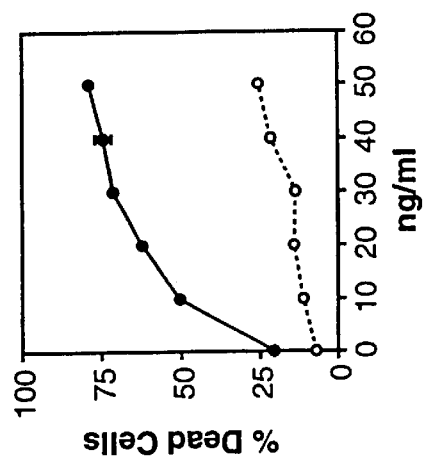
Figure 9A(2)
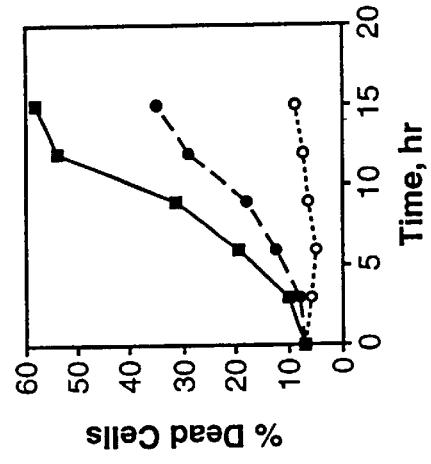
Figure 9B(2)

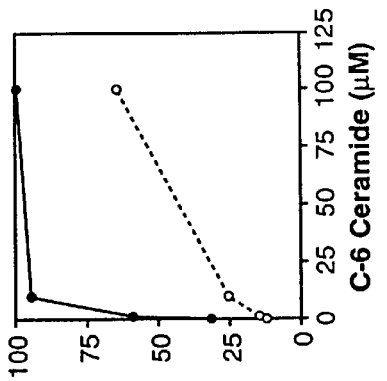
Figure 10A(4)
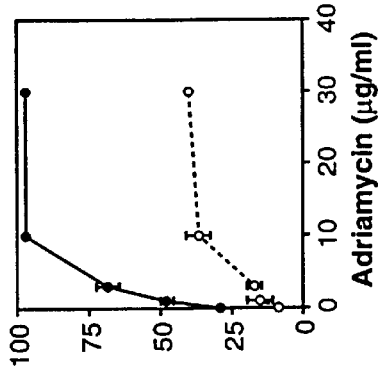
Figure 10A(3)
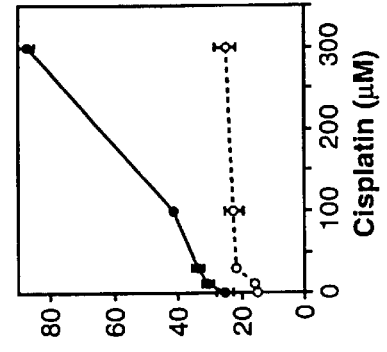
Figure 10A(2)
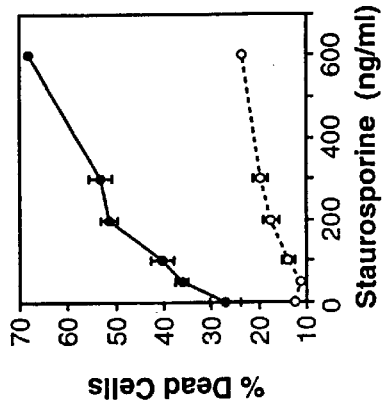
Figure 10A(1)
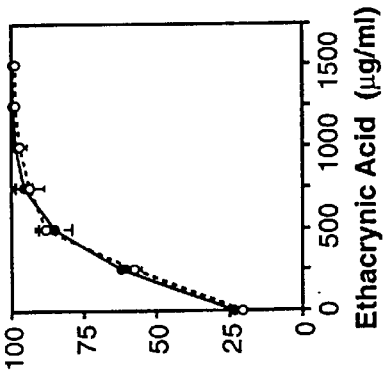
Figure 10B(2)
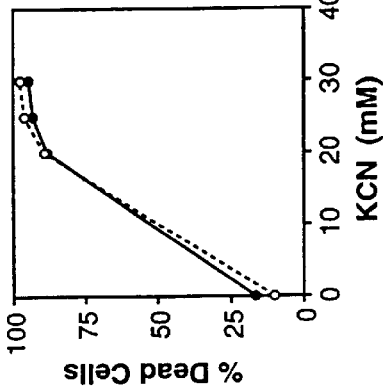
Figure 10B(1)

BAK PROMOTER EXPRESSION SYSTEM

CROSS-REFERENCE TO RELATED APPLICATIONS

This application is a 371 of PCT/US98/02845, filed Feb. 17, 1998, which claims priority to United States Provisional Applications Number 60/038,412, filed Feb. 18, 1997.

STATEMENT OF RIGHTS TO INVENTIONS MADE UNDER FEDERALLY SPONSORED RESEARCH (Not Applicable)

TECHNICAL FIELD

The present invention relates to regulatory elements that are linked to a gene involved in apoptosis. The invention further relates to methods for identifying agents that modulate expression of a gene involved in apoptosis.

BACKGROUND ART

Apoptosis, or programmed cell death, is a normal physiologic process that leads to individual cell death. This process of programmed cell death is involved in a variety of normal and pathogenic biological events and can be induced by a number of unrelated stimuli. Changes in the biological regulation of apoptosis also occur during aging and are responsible for many of the conditions and diseases related to aging. Recent studies of apoptosis have implied that a common metabolic pathway leading to cell death may be initiated by a wide variety of signals, including hormones, serum growth factor deprivation, chemotherapeutic agents, ionizing radiation and infection by human immunodeficiency virus (HIV). Wyllie (1980) *Nature* 284:555–556; Kanter et al. (1984) *Biochem. Biophys. Res. Commun.* 118:392–399; Duke and Cohen (1986) *Lymphokine Res.* 5:289–299; Tomei et al. (1988) *Biochem. Biophys. Res. Commun.* 155:324–331; Kruman et al. (1991) *J. Cell. Physiol.* 148:267–273; Ameisen and Capron (1991) *Immunology Today* 12:102; and Sheppard and Ascher (1992) *J. AIDS* 5:143. Agents that modulate the biological control of apoptosis thus have therapeutic utility in a wide variety of conditions.

Apoptotic cell death is characterized by cellular shrinkage, chromatin condensation, cytoplasmic blebbing, increased membrane permeability and interchromosomal DNA cleavage. Kerr et al. (1992) *FASEB J.* 6:2450; and Cohen and Duke (1992) *Ann. Rev. Immunol.* 10:267. The blebs, small, membrane-encapsulated spheres that pinch off of the surface of apoptotic cells, may continue to produce superoxide radicals which damage surrounding cell tissue and may be involved in inflammatory processes.

While apoptosis is a normal cellular event, it can also be induced by pathological conditions and a variety of injuries. Apoptosis is involved in a wide variety of conditions including but not limited to, cardiovascular disease; cancer regression; immune disorders, including but not limited to systemic lupus erythematosus; viral diseases; anemia; neurological disorders; diabetes; hair loss; rejection of organ transplants; prostate hypertrophy; obesity; ocular disorders; stress; aging; and gastrointestinal disorders, including but not limited to, diarrhea and dysentery.

In Alzheimer's disease, Parkinson's disease, Huntington's chorea, epilepsy, amyotrophic lateral sclerosis, stroke, ischemic heart disease, spinal cord injury and many viral infections, for example, abnormally high levels of cell death occur. In at least some of these diseases, there is evidence that the excessive cell death occurs through mechanisms consistent with apoptosis. Among these are 1) spinal cord injury, where the severing of axons deprives neurons of neurotrophic factors necessary to sustain cellular viability; 2) stroke, where after an initial phase of necrotic cell death due to ischemia, the rupture of dead cells releases excitatory neurotransmitters such as glutamate and oxygen free radicals that stimulate apoptosis in neighboring healthy neurons; and 3) Human Immunodeficiency Virus (HIV) infection, which induces apoptosis of T-lymphocytes.

In contrast, the level of apoptosis is decreased to abnormal levels in cancer cells, which allows the cancer cells to survive longer than their normal cell counterparts. As a result of the increased number of surviving cancer cells, the mass of a tumor can increase even if the doubling time of the cancer cells does not increase. Furthermore, the high level of expression in a cancer cell of the bcl-2 gene, which is involved in regulating apoptosis and, in some cases, necrotic cell death, renders the cancer cell relatively resistant to chemotherapeutic agents and to radiation therapy.

It is convenient to divide the process of physiological cell death into phases. Vaux and Strasser (1996) *Proc. Natl. Acad. Sci.* 93:2239–2244. The earliest phase is the stimulus that provokes the apoptotic response. This may be an external signal delivered through surface receptors or may originate inside the cell from the action of a drug, toxin, or radiation. The next phase includes detection of this signal or metabolic state and transduction of the signal. Signal transduction pathways send this message to the cell death effector machinery. The effector phase is the third part of the cell death mechanism and includes the proteases that are activated during apoptosis, as well as their positive and negative regulators. The fourth phase of cell death is the postmortem phase, in which the cell's chromatin condenses and its DNA is degraded.

The activation or signaling phase of cell death encompasses a great variety of signal transduction pathways that mediate signals from outside the cell, as well as others that originate inside the cell. Two members of the TNF superfamily of receptors, TNFR 1 and CD95, when bound to their respective ligands, TNF-I and CD95L (FasL) can rapidly transduce an apoptotic cell death signal (6–8). Nagata and Golstein (1995) *Science* 267:1449–1456; Cleveland and Ihle (1995) *Cell* 81:479–482; Schutze-Osthoff (1994) *Trends Cell Biol.* 4:421–426. Cell death induced by the CD95/CD95L system is important for the elimination of potentially autoreactive peripheral T cells and contributes to T cell-mediated cytoxicity, whereas the TNFR I/TNF-I system plays a critical role in host defense against microorganisms and their pathogenic factors.

In recent years, a family of proteins has been discovered that controls apoptosis. The prototype of this family is Bcl-2, a protein that inhibits most types of apoptotic cell death and is thought to function by regulating an antioxidant pathway at sites of free radical generation. Hockenbery et al. (1993) *Cell* 75:241–251. Together, the Bcl-2 family of proteins are important intracellular modulators of apoptosis and can be divided into two groups based on their effect on apoptosis. Thus, in a general sense, Bcl-2, Bcl-$x_L$, Mcl-1, BHRF-1 and E1B19K are cell death inhibitors (anti-apoptotic), while Bak, Bax and Bcl-$x_S$ accelerate cell death (pro-apoptotic).

Bcl-2 family members are generally localized to the outer mitochondrial membrane, the nuclear membrane and the endoplasmic reticulum, where they associate with membranes by virtue of their C-terminal hydrophobic tail. All members of the family have two highly conserved regions, called BH1 and BH2, that permit specific interactions between two members to form stable dimers. Their mechanism of action is presently unclear; however, it is known that the ratio of anti-apoptotic to pro-apoptotic Bcl-2 family members in a cell is critical to the cell's survival following initiation of an apoptotic signal.

Bak is a member of the Bcl-2 family and is expressed in heart and other tissues. Bak protein is capable of either killing cells, or actively protecting cells from cell death, depending on how this protein interacts with other cellular proteins. Bcl-2 family members are extremely important in determining the fate of a cell following an apoptotic signal, and Bak may be the most important in the major organs such as heart. In the treatment of heart disease, viral infection and cancer, modulation of the expression of genes encoding proteins that control apoptosis is a major focal point.

Interferons (IFN) were originally discovered in the late 1950s as substances produced in animals infected with viruses that could elicit protection against subsequent viral infection. Isaacs and Lindenmann (1957) *Proc. Royal Soc. Lond. (Biol.)* 147:258–267. This activity was shown to reside in a group of functionally related polypeptides, IFNα, -β and -γ, factors which were further discovered to possess a broad range of biological activities in addition to their antiviral action. IFNα and -β, collectively known as the type I IFN, are synthesized by almost any nucleated cell in response to viral infection and function by binding to common receptors on the surfaces of target cells. IFNγ, referred to as type II IFN, is structurally unrelated to IFNα or -β, is synthesized specifically by activated T cells and natural killer cells, and recognizes cell-surface receptors distinct from those recognized by the type I IFN. Despite their different structures and receptor-binding activities, the type I and type II IFN function in a very similar manner to influence a broad range of biological functions including the modulation of the immune response, inflammation, hematopoiesis, cell proliferation and differentiation. DeMaeyer and DeMaeyer-Guignard (1988) *Interferons and Other Regulatory Cytokines.* Wiley, N.Y.

The diverse effects of IFN are mediated by their binding to specific cell-surface receptors, activation of signal-transducing molecules and the consequent modulation of gene expression. The type I and type II IFNs produce distinct, though partially overlapping, effects on cells. The initial transmission of the IFN signal to the nucleus involves proteins that function in cooperation with one another. These include the Stat (signal transducer and activator of transcription) proteins and ISGF3γ (IFN-stimulated gene factor 3γ polypeptide).

In response to type I IFN, the 113 kDa protein Stat2, the 91 kDa protein Stat1α and the 84 kDa Stat1β become tyrosine phosphorylated. These proteins combine with the 48 kDa ISGF3γ to form IFN-stimulated gene factor 3 (ISGF3), a multimeric complex that translocates to the nucleus and displays a distinct DNA-binding specificity for the IFN-stimulated response element (ISRE) found in the promoters of IFNα-stimulated genes. Darnell et al. (1994) *Science* 264:1415–1420.

In contrast, IFNγ-inducible genes are activated when Stat1α becomes tyrosine phosphorylated and forms homodimers, termed GAF for IFNγ-activated factor, which are capable of binding to the IFNγ-responsive element termed the gamma-activated site (GAS). The two complexes, ISGF3 and GAF, recognize different sequences in the promoters of type I and type II IFN, respectively and are integral components of the system by which IFN stimulation received at the cell surface is translated into changes in gene transcription in the nucleus.

While the ISGF-3 and GAF are responsible for the initial transmission of the IFN signal to the nucleus, the proper regulation of the broad range of genes induced by the interferons involves other transcription factors as well. These include the IFN regulatory factors, or IRFs.

IRF-1, IRF-2 and IRF-3 have been identified as DNA-binding factors that function as regulators of both type I and type II inducible genes. These transcription factors are structurally related, particularly in their N-terminal regions that confer DNA binding specificity. The IRF also show significant amino acid sequence identity to ISGF3γ, the DNA binding component of the complex that recognizes ISRE in IFN-inducible genes and to ICSBP, which is expressed only in cells of lymphoid origin and which binds the ISRE of IFN-inducible genes in these cells. Au et al. (1995) *Proc. Natl. Acad. Sci.* 92:11657–11661. In addition, both IRF-1 and IRF-2 bind to the same sequence within the promoters of IFN-α and IFN-β genes. Harada et al. (1989) *Cell* 58:729–739. The IRF and ISGF3 have also been shown to bind to overlapping sequences in the promoters of many IFNα/β-inducible genes. Tanaka et al. (1993) *Mol. Cell. Biol.* 13:4531–4538. IRF-1 functions as an activator of interferon transcription, while IRF-2 binds to the same cis elements and represses IRF-1 action. IRF-1 and IRF-2 have been reported to act in a mutually antagonsitic manner in regulating cell growth: overexpression of the repressor IFR-2 leads to cell transformation, while concomitant overexpression of IRF-1 causes reversion. In addition to being a regulator of cell growth, IRF-1 is also a key transcription factor in the regulation of apoptosis. Taniguchi et al. (1995) *J. Cancer Res. Clin. Oncol.* 121:516–520; Tamura et al. (1995) *Nature* 376:596–599; Tanaka et al. (1994) *Cell* 77:829–839.

When normal embryo fibroblasts expressing activated c-H-ras were cultured in low serum or treated by anticancer drugs or ionizing radiation they were observed to lose viability by a process characteristic of apoptosis. In contrast, when IRF-1-/-fibroblasts expressing activated c-H-ras were subjected to the same treatment, the cells survived. Tanaka et al. (1994) *Cell* 77:829–839. The tumor suppressor p53 has been shown to regulate apoptosis in thymocytes, while in mitogen-activated mature T lymphocytes, DNA-damage-induced apoptosis was found to be dependent on IRF-1. Tamura et al. (1995) *Nature* 376:596–599. Clinical studies indicate that IRF-1 may function as an anti-oncogene in vivo, preventing the development of some forms of human leukemia. In a study of 13 patients with leukemia or myelodysplastic syndrome who exhibited cytogenetic abnormalities in the 5q31.1 chromosomal region, IRF-1 was the only gene found to be consistently deleted or rearranged in either or both alleles. Willman et al. (1993) *Science* 259:968–971. Splicing aberrations in the IRF-1 gene also occur at high frequency in patients with leukemia or myelodysplastic syndrome. Harada et al. (1993) *Oncogene* 9:3313–3320.

Treatment of cells with IFN-γ can render them susceptible to apoptotic stimuli. For example, various cell lines display an increased sensitivity to cytotoxic signalling through TNFR 1 or CD95 following treatment with IFNγ. Yonehara et al. (1989) *J. Exp. Med.* 169:1747–1756; Fransen et al. (1986) *Eur. J. Cancer and Clin. Oncol.* 22:419–426; Tsujimoto et al. (1986) *J. Immunol.* 136:2441–2444. The human colon adenocarcinoma cell line, HT29, is particularly responsive to IFNγ, which markedly increases its sensitivity to TNF-I as well as anti-Fas antibodies (Ab) mediated cytotoxicity. The IFN-γ-induced sensitivity of HT29 cells to TNF-I or anti-Fas Ab mediated cell death has been attributed to the upregulation of CD95 and TNFR 1, which also occurs during IFN-γ treatment. However, since TNF and anti-Fas Ab induce cell death by apoptotic mechanisms, it is possible that other pro-apoptotic gene products are upregulated by IFNγ, or anti-apoptotic gene products are downregulated, thus priming the cells for programmed cell death following a variety of apoptotic stimuli.

The ability to manipulate the mechanism by which the genes involved in cell death are regulated would provide physicians with a potential target for therapies aimed at ameliorating the effects of diseases that are characterized by abnormal levels of cell death and also would allow for the development of methods to identify agents that can effectively regulate, for example, apoptosis in a cell. However, the mechanisms by which these genes are regulated in a cell have not yet been fully elucidated. Thus, there exists a need to identify methods to manipulate the regulatory elements for genes involved in apoptosis. The present invention satisfies this need and provides related advantages as well.

All references cited herein, including all U.S. or foreign patents or are hereby incorporated by reference in their entirety.

DISCLOSURE OF THE INVENTION

The present invention provides nucleotide sequences that are gene regulatory elements, which regulate the expression of genes involved in cell death. The invention also provides the bak promotor, which regulates expression of the bak gene or heterologous genes linked to the bak promotor. The invention further provides screening assays for identifying agents such as drugs that effectively modulate expression of a gene that is controlled by a bak promoter and is involved in cell death. The invention also provides methods for modulating the level of apoptosis in a cell, and, specifically, in a mammal.

The present invention encompasses isolated polynucleotides comprising the bak promoter (SEQ ID NO:1) or an active fragment thereof. In one embodiment, the active fragment is positions −1077 to −1055 (positions 2945–2967 of SEQ ID NO:1), −2376 to −2360 (positions 1646–1662 of SEQ ID NO:1), −2984 to −2975 (positions 1038–1047 of SEQ ID NO:1), −3073 to −3064 (positions 949–958 of SEQ ID NO:1), or −2591 to −2549 (positions 1431–1473 of SEQ ID NO:1), of said bak promoter. The present invention encompasses methods for identifying an agent that effectively regulates, increases or decreases, the expression of a gene involved in apoptosis in a cell, comprising the steps of: a) introducing into said cell an isolated polynucleotide comprising a bak promoter or an active fragment thereof and a reporter gene; b) determining the level of expression of said reporter gene in said cell of step (a); c) contacting said cell of step (a) with the agent; and d) identifying an effective agent that regulates, increases or decreases, the expression of said reporter gene. Also encompassed is the effective agent identified according to the above method.

The present invention also encompasses methods of reducing or inhibiting the level of apoptosis in a cell, and specifically, methods of treating a patient having a disease characterized by an abnormal level of apoptosis, comprising administering to the cell or patient the effective agent identified above.

The invention also encompasses methods of reducing or preventing toxicity of a normal cell in a patient receiving therapy, including, but not limited to chemotherapy or radiotherapy, comprising administering to the patient a pharmaceutically acceptable composition comprising the effective agent identified above.

BRIEF DESCRIPTION OF THE DRAWINGS

FIGS. 1A and B show the sequence of the bak gene promoter region, consisting of sequence positions −1 to −4021 relative to the translation initiation codon Met1 (SEQ ID NO:1). Also shown are the first 15 amino acids encoded by exon 2 (SEQ ID NO:2). FIG. 1B represents positions −1061 to 45 and contains the region omitted from FIG. 1A (as represented on FIG. 1A as a dotted line). The nucleotide sequence shown in FIG. 1B represents positions 3031–4066 of SEQ ID NO:1. Also shown in FIG. 1B are the first 15 amino acids encoded by exon 2 (SEQ ID NO:2).

FIGS. 2A–2C. FIGS. 2A and 2C are photographs of radiolabeled acrylamide gels showing results of primer extension reactions using the primer PER14 (FIG. 2A). The 1.8 kb NotI/BamHI promoter containing gene fragment was included as a template to perform a sequencing reaction. FIG. 2B (left panel) is a photograph of an ethidium bromide stained acrylamide gel showing the 814 base pair PCR product generated from primers P1 and P0. Subsequent Southern blot analysis of the gel (FIG. 2B, right panel) using primer P3 as a probe.

FIG. 5B), indicating that IRF1, IRF2 and ISGF3γ bind specifically to the bak ISRE following IFN-γ treatment.

FIGS. 7A–7B depict the results of EMSA and gel supershift analyses which show that antibodies to p50 and p65 NFκB proteins bind to complexes formed between Bak promoter κB1 oligonucleotide (SEQ ID NO:4) and factors present in nuclear extracts from HT29 cells treated with either IFN-γ or poly (I-C), and the that same factors bind to κB2 following poly (I-C) but not IFN-γ treatment.

FIGS. 8-1, 8-2, 8-3, and 8-4 show the relative CAT activity measured in HeLa cells co-transfected with pSV-β-Gal and one of the following plasmids: 1) pCATbasic, the control vector which lacks promoter and enhancer sequences; 2) 2.0 pBak, 1.6 pBak or 0.7 pBak, containing 2.0 kb, 1.6 kb or 0.7 kb of the bak gene promoter region, respectively, subcloned upstream of CAT in the pCAT basic vector.

FIGS. 9A(1), 9A(2), 9B(1), and 9B(2) show the dose-dependence and kinetics of anti-Fas antibody- and TNF-induced death of HT29 cells with and without IFN-γ pre-treatment.

FIGS. 10A(1), 10A(2), 10A(3), 10A(4), 10B(1), and 10B(2) show the dose-dependence of HT29 cell death induced by pro-apoptotic (FIG. 10A) and pro-necrotic (FIG. 10B) agents.

FIG. 15B shows the binding activity of Bak and Bax p53 sites in the presence of nuclear extract of HT29 cells, treated or not treated with IFN-γ.

MODES FOR CARRYING OUT THE INVENTION

Figure 3:
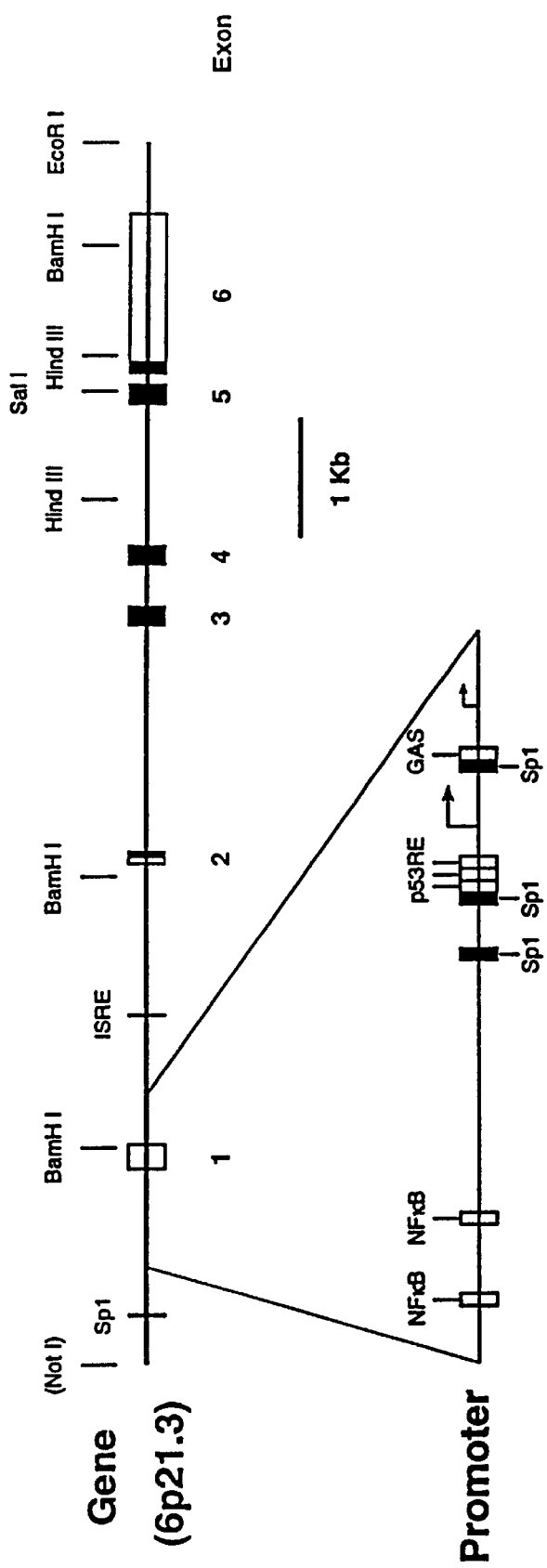
FIG. 3 shows the organization of the bak gene, consisting of six exons (solid rectangles, coding regions; open rectangles, non-coding regions). Also shown are consensus NFκB, p53, Sp1 and GAS sites. Bent arrows represent transcriptional start sites.

The present invention provides isolated polynucleotide sequences, isolated from the bak gene, that act to regulate the transcription of genes involved in apoptosis. These transcriptional regulatory elements are of use in controlling the transcription of polynucleotide sequences to which they are operably linked, and thus they may also lend a level of control to the expression of genes from recombinant molecules. A regulatory element can be characterized, in part, by its being linked to a gene, the expression of which it regulates, and by its being activated due to binding or release of one or more trans-activating factors.

Techniques for polynucleotide manipulation useful for the practice of the present invention are described in a variety of references, including but not limited to, *Molecular Cloning: A Laboratory Manual,* 2nd Ed., Vol. 1–3, eds. Sambrook et al. Cold Spring Harbor Laboratory Press (1989); and *Current Protocols in Molecular Biology,* eds. Ausubel et al., Greene Publishing and Wiley-Interscience: New York (1987) and periodic updates.

The native bak promoter confers transcriptional regulation on the bak gene, which has been described in PCT Publication No. WO 95/15084. As used herein, the "bak promoter" is an isolated polynucleotide having the sequence shown in FIGS. 1A and 1B (SEQ ID NO:1). As used herein, the term "bak promoter" means the nucleotide sequence shown in FIGS. 1A and 1B (SEQ ID NO:1) or active fragments thereof, which can bind a protein or proteins and can confer regulatory activity upon a gene. One skilled in the art would know methods such as those described in Example 7 for identifying active fragments of the bak promoter. For example, a 0.7 kb region upstream of the bak gene has basal promoter activity, but is IFN-γ independent. Upregulation of bak expression in HeLa cells in response to IFN-γ requires both the 1.6 kb (1.6 pBak) upstream region containing GAS and an intron 1 region containing the ISRE.

Generally, methods of detecting promoter functionality are known in the art (see, for example *Molecular Cloning: A Laboratory Manual,* 2nd Ed., Vol. 1–3, eds. Sambrook et al. Cold Spring Harbor Laboratory Press (1989)), and include, for example, the measurement of transcription of mRNA or the expression of a polypeptide from a reporter gene which requires the addition of a functional promoter. While the nucleotide sequence of the promoter (including promoter elements) are given in FIGS. 1A and 1B, it is recognized that nucleotide substitutions can be made which do not affect the promoter or promoter element function. The present invention emcompasses such nucleotide sequences.

In one aspect, the present invention provides an IFN-γ-response element (ISRE), located in the first intron of bak, and a gamma interferon-activated sequence (GAS), which are bound by trans-activating factors. For example, a polynucleotide corresponding to the ISRE (SEQ ID NO:3) binds in vitro to the trans-activating factor IRF-1, IRF-2 and ISGF3γ, and a polynucleotide corresponding to GAS binds STAT1 following INF-γ activation.

Various genes encoding proteins such as Bcl-2, Bcl-2-related proteins such as Bak and ICE and related proteins are involved in the process of cell death. As used herein, the term "cell death" is used to include cell death resulting from various processes such as apoptosis. Reference to "a gene involved in cell death" is meant to include a gene that encodes a protein required for the initiation or continuation of the process of cell death such as apoptosis, which occurs in many cell types as a result of development, damage or disease.

As used herein, the term "operably linked" refers to a juxtaposition wherein the components so described are in a relationship permitting them to function in their intended manner. A control sequence "operably linked" to another control sequence and/or to a coding sequence is ligated in such a way that transcription and/or expression of the coding sequence is achieved under conditions compatible with the control sequence.

The term "polynucleotide" as used herein refers to a polymeric form of nucleotides of any length, either ribonucleotides or deoxyribonucleotides. Thus, this term includes double- and single-stranded DNA and RNA. One skilled in the art would recognize that point mutations and deletions can be made to the bak promoter sequences disclosed herein without altering the ability of the sequence to activate transcription. In addition, active fragments of bak promoter can be obtained. For example, Example 7 provides methods that demonstrate that active fragments of the bak promoter confer up-regulation in response to IFN-γ on a heterologous gene. Similar methods can be used for identifying other active fragments of the bak promoter. Other methods for identifying an active fragment of the bak promoter are routine and well known in the art. For example, overlapping fragments of the bak promoter can be synthesized and cloned into the vector described in Example 7 to determine active bak promoter fragments. Similarly, point mutations can be introduced into the disclosed bak promoter sequences using, for example, site-directed mutagenesis or by synthesizing sequences having random nucleotides at one or more predetermined positions.

The invention includes as an embodiment an isolated polynucleotide comprised of a bak promoter or active fragment thereof. These isolated polynucleotides contain less than about 50%, preferably less than about 70%, and more preferably less than about 90% of the chromosomal genetic material with which the bak promoter is usually associated in nature. An isolated polynucleotide "consisting essentially of" a bak promoter lacks other promoters derived from the chromosome on which bak is located. This terminology of "isolated" and "consisting essentially of" is analogously applicable to a bak enhancer and bak repressor elements. For example, an isolated polynucleotide consisting essentially of a bak enhancer or repressor lacks other enhancers or promoters, respectively, located on the chromosome on which bak is located.

Isolated polynucleotides comprised of or consisting essentially of a bak promoter, bak enhancer, bak repressor or active fragments thereof, may be prepared by techniques known in the art (e.g., Sambrook, et al.). These techniques include, for example, using the sequence information provided herein to provide primers and probes to amplify by PCR specific regions of bak genomic clones, or by chemical synthesis, or by recombinant means.

The term "recombinant polynucleotide" as used herein intends a polynucleotide of genomic, cDNA, semisynthetic, or synthetic origin which, by virtue of its origin or manipulation: (1) is not associated with all or a portion of a polynucleotide with which it is associated in nature; or (2) is linked to a polynucleotide other than that to which it is linked in nature; or (3) does not occur in nature.

A recombinant polynucleotide comprised of a bak promoter or active fragment thereof, as well as those which may be comprised of other bak transcriptional regulatory elements described herein, may be prepared by any technique to those of skill in the art using the sequence information provided herein.

A recombinant polynucleotide comprised of a bak promoter may also be comprised of a coding sequence to which the promoter is operably linked, causing transcription of the coding sequence under the control of the promoter. Coding sequences may encode either homologous or heterologous polypeptides. However, they may also encode other moieties which are desirable in their transcribed form. For example, coding sequences may encode, inter alia, decoy polynucleotides that bind to transcription factors, anti-sense RNAs, and a variety of polypeptides that are of interest (e.g. viral proteins to serve as intracellular vaccines, proteins that serve as markers, etc.), polypeptides for commercial purposes that are to be expressed in cells that express bak proteins, and particularly proteins that are of use in gene therapy.

The invention further encompasses the base pairs important in DNA-protein interaction. Such base pairs can also be elucidated. In this manner, genomic fragments containing the nucleotide −1 to −4021 (positions 1–4021 of SEQ ID NO:1) sequence and fragments containing other areas of interest may be employed in in vitro footprinting experiments (Galas et al. (1981) *Nucleic Acids Res.* 9:6505–6525). Isolated restriction fragments are radiolabeled and subsequently incubated with nuclear extracts made with established techniques (for example, Dignam et al. (1983) *Nucleic Acids Res.* 11:1465–1489). Nuclear extracts (containing DNA binding proteins) can be made from any suitable cell. Labeled DNA fragments are incubated with the nuclear extracts, digested with DNAse I, and electrophoresed on a denaturing polyacrylamide gel. DNA binding proteins in the cell extract bind to their recognition sequence contained in the labeled restriction fragment, and protect the DNA from digestion by the DNAse. Regions of protection delineate the binding site.

The term "polypeptide" refers to a polymer of amino acids and does not refer to a specific length of the product; thus, peptides, oligopeptides, and proteins are included within the definition of polypeptide. This term also does not refer to or exclude post-expression modifications of the polypeptide, for example, glycosylations, acetylations, phosphorylations and the like. Included within the definition are, for example, polypeptides containing one or more analogs of an amino acid (including, for example, unnatural amino acids, etc.), polypeptides with substituted linkages, as well as the modifications known in the art, both naturally occurring and non-naturally occurring.

The bak regulatory sequences described herein can be used to control the transcription and/or expression of linked coding sequences.

Promoter elements of the present invention can also be utilized to direct expression of heterologous promoters. For example, the sequences of the bak promoter between about base pair −4021 (position 1 of SEQ ID NO:1) and about −1 (positions 1–4021 of SEQ ID NO:1) can be used to modulate the rate of transcription in response to IFNγ.

It is recognized that other elements or nucleotide sequences within the bak promoter region, including the first intron, may be important for expression. The present invention encompasses such elements. Further, specific nucleotides or regions within the promoter elements may be identified as necessary for regulation. These regions of nucleotides may be located by fine structural dissection of the elements by analyzing the functional capacity of a large number of promoter mutants. Single base pair mutations can be generated utilizing polymerase chain reaction (PCR) technology. U.S. Pat. No. 4,683,202. Mutated promoter regions can be cloned back into reporter constructs using standard techniques and evaluated by transfection into appropriated cells and assayed for reporter gene function. This analysis will also identify nucleotide changes which do not affect promoter function.

The invention also includes recombinant host cells comprised of any of the above described polynucleotides that contain a bak promoter and/or bak enhancer and/or bak repressor. The polynucleotides may be inserted into the host cell by any means known in the art. As used herein, "recombinant host cells", "host cells", "cells", "cell lines", "cell cultures", and other such terms denoting microorganisms or higher eukaryotic cell lines cultured as unicellular entities refer to cells which can be, or have been, used as recipients for recombinant vector or other transfer DNA, and include the progeny of the original cell which has been transformed. It is understood that the progeny of a single parental cell may not necessarily be completely identical in morphology or in genomic or total DNA complement as the original parent, due to natural, accidental, or deliberate mutation.

"Transformation", as used herein, refers to the insertion of an exogenous polynucleotide into a host cell, irrespective of the method used for the insertion, for example, direct uptake, transduction, f-mating or electroporation. The exogenous polynucleotide may be maintained as a non-integrated vector, for example, a plasmid, or alternatively, may be integrated into the host cell genome.

Also included within the invention are antisense polynucleotides and decoys to the promoter, enhancer, and repressor elements of the bak gene. These polynucleotides may be prepared by a variety of techniques known in the art, including chemical synthesis and recombinant technology. Antisense polynucleotides to the transcription elements may be used in the regulation of transcription of a polynucleotide sequence to which the regulatory element is operably linked, including the polypeptide encoded by the bak gene.

The polynucleotide sequences described herein are also useful for identifying factors which bind specifically to the bak promoter. For example, binding activity in nuclear extracts may be determined using electrophoretic mobility shift assays (EMSA). The technology for performing EMSAs is well described in the literature. Fried and Crothers (1981) *Nucl. Acids Res.* 9:6505–6525; Revzin (1989) *Biotechniques* 7:346–355; Strauss and Varshavsky (1984) *Cell* 37:889–901. Either $^{32}$P-labelled restriction fragments or annealed pairs of complementary oligonucleotides are incubated with nuclear extracts and poly d(I-C) in a binding buffer, and the products of this reaction electrophoresed on a non-denaturing polyacrylamide gel. The location of the DNA fragment on the gel as determined with autoradiography is retarded in cases where protein has bound to the DNA. The extent of the retardation is a relative function of the size of the protein, and it has thus been possible to distinguish two or more different proteins present in different tissues binding to a single sequence.

The bak promoter can further be used in assays designed to screen for agents that modulate bak promoter function, and which therefore may modulate the production of Bak protein. The bak promoter, or the ISRE in the first intron, can be inserted into vectors and can be operably linked to a reported gene. Host cells are then transfected or transformed with expression vectors and cultured in conventional nutrient media modified as appropriate for inducing promoters, selecting transformants, or amplifying the genes encoding the desired sequences. Heterologous DNA may be introduced into host cells by any method known in the art, such as transfection with a vector encoding a heterologous DNA by the calcium phosphate coprecipitation technique, by electroporation or by lipofectin-mediated transfection. Numerous methods of transfection are known to the skilled worker in the field. Successful transfection is generally recognized when any indication of the operation of this vector occurs in the host cell. Transformation is achieved using standard techniques appropriate to the particular host cells used. The product of the reporter gene can be detected by an appropriate assay, thus allowing identification of an agent that modulates the activity of the bak promoter.

Cell-based screening assays can be designed, e.g., by constructing cell lines in which the expression of a reporter protein, i.e., an easily assayable protein, such as β-galactosidase, chloramphenicol acetyltransferase (CAT), green fluorescent protein (GFP) or luciferase, is dependent on the function of a bak promoter. For example, a DNA construct comprising a bak promoter is operably linked to a gene encoding GFP. The resulting DNA construct comprising the GFP-encoding DNA is stably transfected into a host cell. The cell may be exposed simultaneously to a compound that induces the promoter and a test compound, and, after a time, the cells are assayed for the production of GFP by exciting the fluor at 488 nm and measuring emission at 511 nm (see FIG. 14).

As used herein, the term "reporter gene" means a gene that encodes a gene product that can be identified. Reporter genes include, but are not limited to, chloramphenicol acetyl transferase, β-galactosidase, luciferase and green fluorescence protein. Identification methods for the products of reporter genes include, but are not limited to, enzymatic assays and fluorimetric assays. Reporter genes and assays to detect their products are well known in the art and are described, for example in *Current Protocols in Molecular Biology*, eds. Ausubel et al., Greene Publishing and Wiley-Interscience: New York (1987) and periodic updates.

Cells expressing products of reporter genes under the control of a bak promoter are useful for identifying agents that modulate the activity of a bak promoter. Thus, host cells expressing a reporter gene product under the control of a bak promoter are useful for drug screening and it is a further object of the invention to provide a method for identifying an agent that modulates the activity of a bak promoter. The method includes exposing a cell containing a bak promoter to at least one compound whose ability to modulate the activity of a bak promoter is sought to be determined. The cells are then monitored for changes caused by the modulation.

Assay methods generally require comparison to various controls. A change in bak promoter activity is said to be effected by a test compound if such an effect does not occur in the absence of the test compound.

Ability to regulate a promoter that controls a gene involved in apoptosis-induced cell death provides the potential to control the process of apoptotic cell death in a cell or tissue. Suitable indications for therapeutic use of agents that result in modulation of apoptotic pathways include, but are not limited to, ischemic heart disease, tumors, viral diseases such as HIV infection, neurodegenerative disorders, inflammatory bowel disease, hair loss, and rejection of organ transplants.

The ability to manipulate the regulatory elements involved in the abnormal regulation of cell death in various diseases and the availability of a variety of cell types from patients having such diseases allows for the identification of agents that can be used to effectively treat patients having these diseases. Thus, the invention also provides screening assays for identifying agents such as drugs that effectively modulate expression of a gene that contains a bak promotor or an active fragment thereof.

As used herein, the term "agent" means a biological or chemical compound such as a simple or complex organic molecule, a peptide, a protein or an oligonucleotide. Thus, screening assays provide a method for identifying an "effective agent," which can be used to modulate cell death in a cell in vitro or in a patient.

As used herein, the term "modulate" means that the effective agent can increase or decrease the level of expression of a gene that is involved in cell death and that contains a bak promoter or an active fragment thereof. For example, an effective agent for treating a cancer cell would allow a Bak-deficient cell to behave as if it expressed a wild-type bak apoptosis suppressor and, therefore would increase the level of apoptosis in the cancer cell. Such an effective agent can act in various ways. For example, an effective agent that is a peptide or a protein can modulate bak gene expression by binding to an ISRE or GAS and up-regulating expression of the gene. Alternatively, the effective agent can be a small organic molecule that affects the structure or binding ability of a mutant ISRE or GAS binding protein, such as IRF-1 or STAT1, such that the mutant ISRE or GAS binding protein binds to an ISRE or GAS and modulates the expression of the bak gene.

The following examples are provided to illustrate but not limit the invention.

EXAMPLE 1

Identification and Cloning of a Bak-Specific Intron

It has been shown previously by Southern blot analysis of human/rodent somatic cell hybrid DNA using the bak cDNA probe that three distinct bak genes exist and that they are located on chromosomes 6 (bak), 20 (bak-2) and 11 (bak-3). These same analyses also suggested that the bak gene contained introns and that the bak-2 and bak-3 genes were processed genes lacking introns. Previous attempts to clone the three bak genes using the bak cDNA as a probe resulted in the isolation of several bak-2 and bak-3 genes. The sequencing of these genes confirmed that they were intronless. To clone the bak gene, a bak intron was used as a probe, which would specifically identify the bak gene and not detect bak-2 or bak-3 sequences.

Southern blot analysis suggested that an intron was present between exons encoding the conserved BH2 domain and the transmembrane (TM) domain of the bak gene. This was consistent with the intron/exon organization of other bcl-2 family members (see Cory (1995) *Ann. Rev. Immunol.* 13:513–543). To identify this putative intron from bak, PCR was performed using oligonucleotide primers (1 mM each) encoding a region of the BH2 domain (5'-agatctgaattcCTGTTTGAGAGTGGCATCAATTGG-3') (SEQ ID NO:5) and the TM domain (5'-agatctgcggccgcAGTCATGATTTGAAGAATCTTCGTAC-3') (SEQ ID NO:6); lower case nucleotides represent several restriction endonuclease sites that were added to facilitate subcloning. Template DNA consisted of genomic DNA (0.3 μg) from a hamster/human somatic cell hybrid containing only human chromosome 6 (Coriell Cell Repositories, GM/NA 10629). Conditions for the reaction were as described by the suppliers of the Hot Start/Ampliwax PCR kit (Perkin Elmer Cetus). The PCR product (#105-2) was gel purified, subcloned into pBluescript SK-(Stratagene) and sequenced.

Sequence analysis of #105-2 revealed the expected exon regions of bak and an intron of 126 bp following the codon for amino acid 177 that obeyed the consensus sequence rules at the intron/exon borders for eukaryotic genes (Mount (1982) *Nucleic Acids Res.* 10:459–472). To generate a bak-specific intron probe, an additional PCR reaction was performed as above but with oligonucleotide primers that matched the ends of the intron (5'-agatctgaattcGTGAGTATCCAAGGACTGCAA-3' and 5'-agatctaagcttCTGCCGGGAGAAACAAGGTG-3') (SEQ ID NO:7 and SEQ ID NO:8, respectively), and using the above PCR product, #105-2, as template. The resulting PCR product, i/T3, was subcloned and sequenced as above to confirm that it contained the intron sequence.

EXAMPLE 2

Cloning and Characterization of the Human Bak Gene

The bak-specific intron probe, i/T3, was used to screen a human placental library in the cosmid vector, pWE15. 900,000 clones were screened with the i/T3 probe that was $^{32}$P-labeled according to the method of Feinberg and Vogelstein (1984) *Anal. Biochem.* 137: 266–267. The library was processed and screened under high stringency hybridization and washing conditions as described by Sambrook et al. (1989) *Molecular Cloning*, 2nd edition, Cold Spring Harbor Laboratory Press. Two double positive clones were identified (L 1a and L 2a) and further purified by replating and screenings as above. Plasmid DNA was purified using the Wizard Maxiprep DNA Purification System as described by the supplier (Promega Corp.) and analyzed by restriction enzyme mapping. Each clone displayed the same restriction pattern and thus were identical clones.

EXAMPLE 3

Identification and Characterization of the Bak Gene Promoter

To identify the promoter region of the bak gene, Southern blot analysis was performed using a $^{32}$P-labeled 5' untranslated probe from the bak cDNA. This identified a 1.8 kb NotI/BamHI DNA fragment that was subcloned and sequenced (FIGS. 1A and 1B). The BamHI site is shown in italics (nucleotides −2272 to −2267). The NotI site (nucleotides −4029 to 4022) is not shown because it is derived from the cosmid vector sequence (pWE15). Also shown in FIGS. 1A and 1B is intron 1 (from nucleotide −2260 to −992 and −101 to −32) and exon 2 (from nucleotide −31 to 45). The identification, cloning and sequencing of these regions is described in Example 4. Nucleotides are numbered relative to the first ATG codon in exon 2. Nucleotides in exons are denoted by upper case letters. Contained within this sequence are several transcriptional activator sites (indicated in bold below the nucleotide sequences) including the following. 1) Two NFκB sites are located at nucleotides −3073 to −3064 (κB1) and nucleotides −2984 to −2975 (κB2). NF-κB is involved in transducing multiple signals from a variety of cytokines, cell-damaging agents and viruses (see Thanos and Maniatis (1995) *Cell* 80:529–532.). 2) Three clustered p53 response elements are located at nucleotides −2586 to −2577 (perfect 10 of 10 match with consensus sequence as defined by El-Deiry et al. (1992) *Nature Genet.* 1:45–49; solid underline), nucleotides −2573 to −2564 (8 of 10 match; solid underline) and nucleotides −2558 to −2549, (7 of 10; broken underline). p53 is a tumor suppressor that functions in part as a transcriptional regulator and is capable of inducing cell cycle arrest at the G1/S border and inducing apoptosis in response to radiation and DNA-damaging chemotherapeutic agents. 3) An ISRE is located at −1077 to −1055. 4) A GAS site is located at nucleotides −2371 to −2360. 5) Four Sp1 sites are located at nucleotides −3593 to −3588, −2627 to −2622, −2591 to −2585 and −2376 to −2360. Sp1 binds to GC-rich segments of DNA upstream of the transcriptional start site and increases the level of transcription (see Dynan and Tjian (1983) *Cell* 35:79–87). Sp1 is a general promoter binding factor necessary for the activation of a variety of genes, including many with TATA-less promoters.

To determine bak transcriptional initiation sites, primer extension reactions were performed as described (Seto et al. (1988) *EMBO J.* 7:123–131) using a $^{32}$P-labeled oligonucleotide complementary to nucleotides −2311 to −2282 (PER 14; double underlined in FIG. 1) and 5 μg of poly (A)$^{+}$ RNA from IFN-γ-treated HT29 cells. To precisely define the location of the start sites, a sequencing reaction was run in parallel (lanes G, A, T and C) using the primer PER 14 and the 1.8 kb NotI/BamHI promoter containing gene fragment, described above, as template. The primer extension reactions are shown in FIGS. 2A and 2C and indicate multiple start sites. These start sites (indicated by upper case letters) and corresponding nucleotides (in parenthesis; numbering corresponds to that of FIG. 1) are shown in bold, upper case letters, marked by asterisks, in FIG. 1. To confirm the start site proximal to the promoter (nucleotide −2507) obtained by primer extension (FIG. 2A), reverse transcription coupled with PCR (RT-PCR) was employed using the primer extension product as template. Two 5' primers were designed that were either upstream or overlapped the transcriptional start site (P2 and P1, respectively, FIG. 1; double underlined). The 3' primer was complementary to nucleotide 674 to 694 of the bak cDNA (numbering from FIG. 1A of Kiefer et al. (1995) *Nature* 374:736–739). A PCR product of approximately the expected size (814 bp) was generated from primers P1 and P0, but not from primers P2 and P0 as shown by the ethidium bromide stained acrylamide gel (FIG. 2B, left panel) and subsequent Southern blot analysis of the gel (FIG. 2B, right panel) using primer P3 as a probe (FIG. 1; double underlined). This result further suggests that the first transcriptional start site (farthest upstream) is at or close to nucleotide −2507 (G). No TATA box was found upstream of this start site or any of the other start sites, indicating that the bak gene contains a TATA-less promoter.

EXAMPLE 4

Intron/Exon Organization of the Bak Gene

To identify the remainder of the bak gene, additional Southern blot analyses of clone L 1a were performed using the complete bak cDNA as a probe. Two BamHI fragments of ~5 kb and 4.4 kb that hybridized to the probe were subcloned and sequenced. Alignment of the bak cDNA with these sequences revealed that the 5 kb fragment contained most of the exons (all of exons 2–5 and most of exon 6) and the 4.4 kb contained the remainder of exon 6. A schematic diagram of the bak gene is shown in FIG. 3. Exons are represented as large rectangles and are numbered (solid, coding regions; open, non-coding regions). Only 900 bp (BamHI-EcoRI) of the 4.4 kb BamHI fragment is shown. Most of the non-coding exon 1 was located on the 1.8 kb NotI-Bam HI promoter fragment described above. The NotI site and the adjacent 20 nucleotides are from the cloning vector pWE15 and are not shown. A region of the promoter has been expanded in FIG. 3 to show, in schematic form, the transcriptional regulatory regions previously described. The bent arrows represent transcriptional start sites identified in Example 3. An additional 2.2 kb intron was found by PCR (using primers based on exon 1 and exon 2 sequences) when it was realized that the 5'-untranslated sequence contained an intron. The intron is almost perfectly flanked by BamHI sites and therefore did not hybridize to the cDNA probe. Contained within this intron is the ISRE. Several clusters of Alu repeats were found in the bak gene including sequences from the Sp, Sx and Sq subfamilies in both positive (+) and negative (−) orientations. Interestingly, the two NFκB sites were located within a Sp(+) Alu repeat. Alu sequences are intermediate repetitive elements of ~300 bp that are interspersed through the human genome and are classified into subfamilies based on their sequence (Jurka and Milosavljevic (1991) *J. Mol. Evol.* 32:105).

EXAMPLE 5

IFN-γ and Poly (I-C) Upregulate Bak Transcription

Figures 4A, 4B:
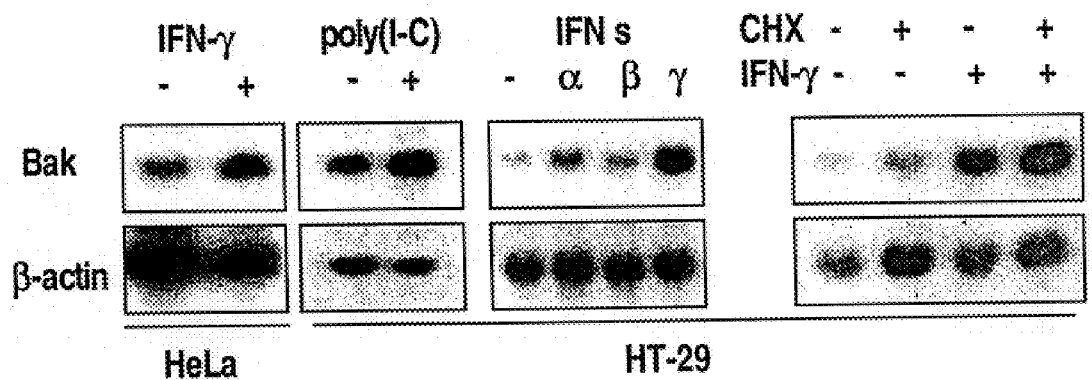
FIGS. 4A–4B depict Northern blot analyses of bak gene expression in HeLa and HT29 cells in response to IFN-α, -β, and -γ, and poly (I-C), and also in IFN-γ-treated HT29 cells in the presence of cycloheximide (CHX).

Identification of GAS and ISRE sites in the promoter region and first intron of the bak gene suggested that bak gene expression may be regulated by interferons. To examine bak gene expression, Northern blot analyses were performed with HT-29 and Hela cells following IFN treatment. Bak mRNA expression following poly (I-C) treatment was also analyzed. Double-stranded deoxyinosine-deoxycytosine copolymer (poly (I-C)) is a synthetic double-stranded RNA (dsRNA) that mimics viral infection. It is a potent inducer of interferon and activator of interferon-induced, dsRNA-dependent enzymes such as PKR and 2',5' oligoadenylate synthetase. These two enzymes are involved in maintaining the anti-viral state (see Jacobs and Langland (1996) *Virology* 219:339–349). For Northern blot analysis, HT-29 cells were treated with either IFN-γ (200 units/ml), poly (I-C) (25 μg/ml in DMRIE-C (Invitrogen)), IFN-α (200 units/ml), IFN-β (500 units/ml, IFN-γ (200 units/ml) and cycloheximide (10 μg/ml) or buffer control (DMRIE-C for poly (I-C) experiments) for 16 hours. HeLa cells were treated with IFN-γ (500 units/ml) or buffer control for 16 hours. Total RNA was isolated from the cells by the single step acid guanidinium thiocyanate/phenol/chloroform extraction method (Chomczynski and Sacchi (1987) *Anal. Biochem.* 162:156–159). RNA samples (20 μg) were fractionated by electrophoresis on 1% agarose-2.2 M formaldehyde gels, transferred to nitrocellulose membranes and then prehybridized and hybridized at 42° C. in a standard solution containing 40% formamide (Sambrook et al. (1989) In: *Molecular Cloning: A Laboratory Manual,* 2nd Ed., Cold Spring Harbor Laboratory, Cold Spring Harbor, N.Y.). Standard high stringency washing conditions were used (0.1× SSC, 0.1% SDS at 65° C.). The bak cDNA probe was excised from the pcDNA3 vector, gel purified and $^{32}$P-labelled as described (Feinberg and Vogelstein (1984) *Anal. Biochem.* 137:266–267). The amount of RNA in each lane was verified by hybridization with a β-actin probe. FIG. 4 shows that IFN-γ treatment moderately upregulates bak mRNA expression in HeLa cells but has a more significant effect in HT-29 cells. Poly (I-C) moderately upregulates bak mRNA levels in HT-29 cells while IFN-α and IFN-β weakly increase bak mRNA levels. Bak mRNA expression is also induced by IFN-γ in the presence of cycloheximide (CHX), indicating that additional protein synthesis is not required. This demonstrates that bak mRNA is directly induced by IFN-γ and does not require de novo synthesis of additional transcriptional activators. These results suggest that some of the antiviral and antigrowth effects of IFN-γ may be realized through the upregulation of Bak which would increase the sensitivity of cells to apoptotic cell death, as described in Example 8. This is consistent with the role of Bak as an antiviral and antigrowth (i.e., tumor suppressor) agent.

EXAMPLE 6

Promoter Elements that Mediate Induction of Bak mRNA Expression by IFN-γ and Poly (I-C)

To examine the transcription factors that specifically bind promoter and neighboring elements of the bak gene and presumably mediate INF-γ and poly (I-C) induction of bak mRNA synthesis, electrophoretic mobility shift and supershift assays were performed. Double-stranded oligonucleotides corresponding to the bak intron 1 ISRE (5' GCAAACTGAAAGTGAAACAGCT 3') (SEQ ID NO:3), the bak promoter GAS (5' CGCCCATTCCTGGAAACTGG 3') (SEQ ID NO:9) and the two bak promoter NFκB sites (κB1: 5' CAGGTTCAAGGGATTCTCCTGCCTCA 3'; κ2: 5' AGTAGAGACGGGGTTTCACCATGTTA 3') (SEQ ID NO:4 and SEQ ID NO:10, respectively) were synthesized. These oligonucleotides were radioactively end-labelled with $^{32}$P-ATP and T4 polynucleotide kinase, and allowed to interact with nuclear extracts prepared from HT-29 cells as described (Bomsztyk, K. et al. *J. Biol. Chem.* 265:9413 (1990)). The cells were pre-treated with INF-α, -β, or -γ, or poly (I-C) as described in Example 5. Binding reactions were carried out in a total volume of 20 μl, containing nuclear extract (10 μg total protein), labeled DNA (50,000 cpm), varying amounts of unlabeled competitor oligonucleotide and poly (I-C) (1 μg) in EMSA buffer (5 mM KCl, 10 mM Tris-HCl (pH 7.5), 1 mM dithiothreitol, 1 mM EDTA, 4% glycerol) for 10 minutes at room temperature. Gel supershift assays were performed as described above, except that antibodies specific for various promoter-binding proteins were added after the initial binding reaction and the mixture was incubated overnight at 4° C. The samples were then fractionated by electrophoresis on a 4% polyacrylamide gel at 10 mA at 4° C. in 0.3×TBE running buffer. The gel was then dried and exposed to x-ray film at −70° C. overnight.

Figure 5A:
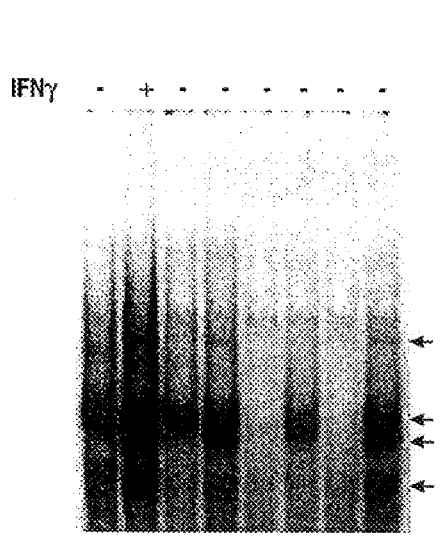
FIGS. 5A, 5B and 5C show the binding of IRF proteins to an oligonucleotide corresponding to bak ISRE (SEQ ID NO:3) following IFN-α, -β, or -γ, or poly (I-C) treatment of HT-29 cells. Also shown is the gel supershift analysis (SS.
Figure 5B:
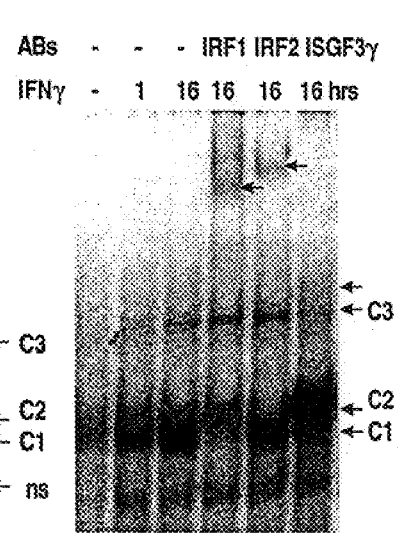
Figure 5C:
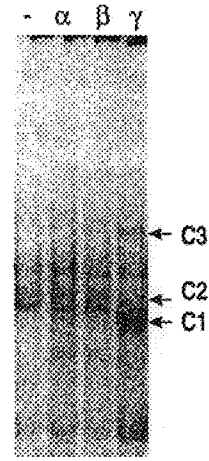

Treatment of HT29 cells with INFγ resulted in enhanced levels of IRF proteins binding to ISRE as shown by the increasing amounts of complexes 1, 2 and 3 (C1, C2 and C3) formed (FIGS. 5, A–C). The complexes were formed as early as 1 hour after addition of INFγ (FIG. 5B). Formation of these complexes was shown to be specific, since the complex formation was efficiently competed by 50-fold excess unlabelled Bak ISRE oligonucleotide (FIG. 5A, oligo s), but not by an oligonucleotide having an unrelated sequence (ns). Specific binding to the complexes was also enhanced following treatment of the cells with poly (I-C) (FIG. 5A). Treatment of the cells with IFN-α or IFN-β did not induce C1 and C3 formation while C2 appears to be unchanged by either treatment (FIG. 5C).

The composition of the proteins in C1–3 was examined using antibodies reactive with specific promoter-binding proteins in gel supershift assays. The supershift experiments (SS) show that at least three proteins of the Interferon Regulatory Factors (IRF) family interact with the Bak ISRE: IRF-1, IRF-2 and ISGF-3γ (FIG. 5B). IRF-1 is a transcriptional activator with tumor suppressor activity. IRF-2 is an antagonistic repressor of IRF-1 and has tumor promoting activity. ISGF3γ is a 48 kd protein that binds to ISRE as part of a heterotrimeric complex. Harada et al. *Cell* 58:729 (1989); Bluyssen et al. *Proc. Natl. Acad. Sci.* 92:5645 (1995).

Figure 6A:
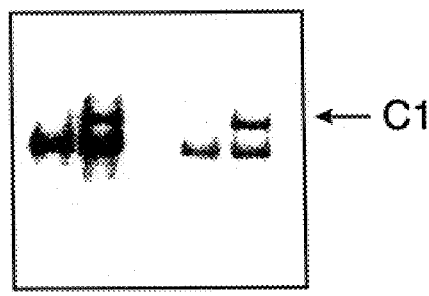
FIGS. 6A–6B show specific binding of STAT1, but not STAT2, to an oligonucleotide corresponding to the Bak GAS (SEQ ID NO:9) following IFN-γ treatment but not following IFN-α or IFN-β treatment.
Figure 6B:
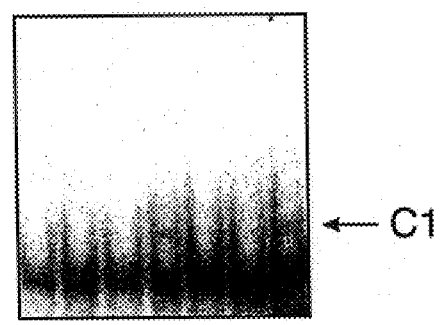

Treatment of HT29 cells with IFN-γ also resulted in protein binding to the GAS as shown by complex 1 (C1) formation (FIG. 6A). The complex was shown to be specific, since the complex formation was efficiently competed by 50-fold excess unlabeled Bak GAS oligonucleotide (FIG. 6A, oligo s), but not by an oligonucleotide having an unrelated sequence (ns). Specific binding to the complex was not observed following treatment of the cells with poly (I-C), IFN-α or IFN-β (FIG. 6B).

The composition of the proteins in the Bak GAS C1 was examined using antibodies reactive with specific promoter-binding proteins in gel supershift assays. The SS experiments show that STAT1 interacts with the Bak GAS (FIG. 6B) as evidenced by disappearance of C1 following treatment with anti-STAT1 antibodies. Anti-STAT2 antibodies did not affect C1 formation and therefore STAT2 is not present in the complex. STAT1 and STAT2 are members of a family of DNA-binding proteins involved in IFN-regulated gene expression. STAT1 is a transcriptional activator that regulates genes that collectively provide innate immunity. Meraz et al. (1996) *Cell* 84:431–442; Durbin et al. (1996) *Cell* 84: 443–450.

NFκB is a member of the Rel family of transcriptional regulatory proteins. Rel family members are activated by a number of agents including bacterial and viral pathogens, immune and inflammatory cytokines and cell damaging agents, and, when bound to κB sites, activate a wide variety of genes including those involved in the immunity and apoptosis. Thanos and Maniatis (1995) *Cell* 80:529–532; Liu et al. (1996) *Cell* 87:565–576.

In addition to inducing binding of IRF family members and STAT1 to the Bak ISRE and GAS, respectively, INF-γ also enhances binding of NFκB family members p50 and p65 to the Bak κB1 site (FIG. 7A, upper panel). This experiment shows that both IFN-γ and poly (I-C) treatment of cells results in the formation of two complexes (C1 and C2) with the Bak κB1 site (FIGS. 7A and B, upper panels). The poly (I-C) response was stronger than that of IFN-γ, as judged by the levels (i.e., band intensities) of C1 and C2. Supershift analysis (SS) indicated that C1 contained a p50 homodimer while C2 contained a p50/p65 heterodimer. In a similar experiment, the Bak κB2 site was shown to form the same two complexes as the KB1 site, although to a lesser extent, following poly(I-C) treatment of cells, but did not form either complex following IFN-γ treatment (FIGS. 7A and B, lower panels).

EXAMPLE 7

Analysis of Bak Promoter Function

Bak promoter function was analyzed in a chloramphenicol acetyl transferase (CAT) reporter gene transient transfection assay. Various DNA fragments of the promoter and 5' regulatory region of the bak gene were subcloned into the pCAT basic plasmid (Promega), as shown schematically in FIG. 8. The relevant transcriptional activator elements and start sites (indicated by arrows) from each construct are also shown. The name of each construct is derived from the length of the region subcloned, e.g. construct 1.6 pBak contains the 1.6 kb fragment of the bak promoter shown. The Bak promoter constructs were co-transfected with the pSV-β-Gal plasmid into HeLa cells using lipofectamine transfection method as described by the supplier (Invitrogen). CAT activity was measured 48 hours after transfection by a CAT immunosorbant assay (ELISA) as described by the supplier (ProMega) and the values were normalized to the β-galactosidase activity. β-galactosidase activity was measured by methods known in the art. The results, shown in FIG. 8, represent the average of two to five independent assays and suggest the following conclusions. 1) The region of the promoter required for basal level transcriptional activity resides a maximum of 700 bp upstream of the start sites and appears to require the NFκB sites. This region is not responsive to IFN-γ activation. 2) IFN-γ activation of bak gene transcription requires both ISRE and GAS. 3) GAS and NFκB sites are insufficient for IFN-γ activation of bak gene transcription.

EXAMPLE 8

Induction of Apoptosis by TNF-α and Anti-Fas Antibody in IFNγ-Treated HT29 Cells The human colon adenocarcinoma line HT29 is relatively insensitive to killing by TNF-α and anti-Fas antibody (Ab), but can be killed by these cytotoxic agents after pretreatment with IFN-γ. For these studies, HT29 cells (ATCC HTB-38) were grown in McCoy's 5a medium supplemented with 10% fetal bovine serum at 37° C. in a humidified 5% $CO_2$ atmosphere. Cells were seeded ($1\times10^5$/ml) in 6 well plates (Corning) for the cell death assay or in flasks for DNA, RNA or protein analysis (see Examples below) and grown to 60–80% confluency. IFN-γ (Boehringer Mannheim) was then added (200 U/ml) and the cells were incubated at 37° C. for 16–24 hr. After washing, cytotoxic agents were added and the cells were incubated an additional 2–24 hours. To measure cell death, non-adherent cells were collected by aspiration and adherent cells were harvested using 0.25% Trypsin/0.05% EDTA. Cells were counted on a Coulter Counter ZM and Coulter Channelyser 256. The percentage of dead cells was calculated as a ratio of detached cells to the total amount of cells per well. For morphological analysis, propidium iodide (1 μg/ml) and Hoechst 33342 (10 μg/ml) were added to wells and the cells were analyzed by luminescence microscopy.

In the dose dependence studies (FIG. 9, upper row), different amounts of anti-Fas Ab (left panels) or TNF-α (right panels) were added to cells untreated (open symbols) or pretreated (closed symbols) with IFNγ. The percentage of dead cells was determined 16 hours later as described above. The lower row presents data on the kinetics of death of HT29 cells pretreated with IFN-γ and then incubated without additions (open circles) or in the presence of 5 ng/ml (closed circles) and 25 ng/ml (closed squares) of anti-Fas Ab or 50 ng/ml TNF-α (closed circles).

Pretreatment of HT29 cells with IFN-γ not only increases their sensitivity to killing by TNF-I and anti-Fas Ab, but also increases their sensitivity in a dose dependent manner to a variety of apoptotic stimuli that act through different mechanisms (FIG. 10A). HT29 cells untreated (open symbols) or pretreated (closed symbols) with IFN-γ were incubated with different cytotoxic agents for 16 hours (panel A) or necrotic agents for 2 hours (panel B). The percentage of dead cells was determined as described above. Staurosporine induces apoptosis by inhibiting protein kinases (Tamaoki and Nakano (1990) *BioTechnology* 8:732–735). Cisplatin causes DNA-DNA and DNA-protein crosslinking while adriamycin inhibits topoisomerase II (Zamble and Lippard (1995) *Trends Biochem Sci.* 20:435–439; Calabresi and Chabner (1990) In: *The Pharmacological Basis of Therapeutics,* Eighth Edition, A. G. Gilman, T. W. Rall, A. S. Nies and P. Taylor, eds. (New York: Pergamon Press), 1202–1263). Ceramide, a bioactive sphingolipid, is a second messenger in apoptotic pathways induced by several different agents, including TNF-I and anti-Fas Ab (Kolesnick and Golde (1994) *Cell* 77:325–328). In these experiments, 8–15% cell death was observed following IFN-γ treatment in the absence of any additional pro-apoptotic stimuli. Thus, it is possible that HT29 cells pretreated with IFN-γ are more sensitive to any cytotoxic agent. However, we found that the sensitivity of HT29 cells to the necrotic agents, potassium cyanide and ethacrynic acid, was identical in IFN-γ treated and untreated cells (FIG. 10, panel B).

Figures 11A, 11B, 11C:
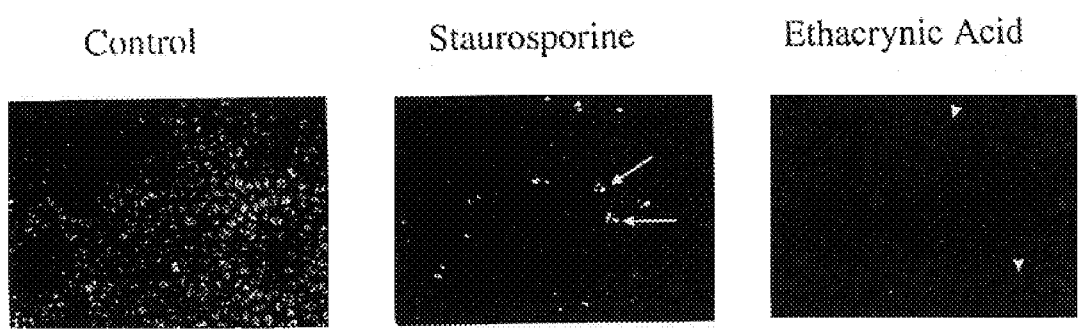
FIGS. 11A–11C show the results of luminescent microscopy of HT29 cells treated with various cytoxic agents.

Several different methods were used to confirm that the agents shown in FIG. 10A induced apoptotic cell death, while the agents shown in FIG. 10B induced necrotic cell death. HT29 cells were pretreated with IFN-γ and then incubated 9 hours with 1 μg/ml staurosporine or 2 hours with 1.5 mg/ml ethacrynic acid. Control cells were only pretreated with IFN-γ. Cells were then were stained with 1 μg/ml PI and 10 μg/ml Hoechst 33342 and analyzed by luminescent microscopy. Luminescent microscopy revealed cells with condensed chromatin, a nuclear morphology characteristic of apoptosis (FIG. 11). Many of the cells with condensed chromatin were impermeable to PI (white arrows) indicating that nuclear changes preceded the increase in outer membrane permeability. In one cell (black arrow) both chromatin condensation and outer membrane permeability had occurred indicating a later stage of apoptosis. In contrast, ethacrynic acid, which induces necrosis, did not induce chromatin condensation (white triangular arrows).

As an additional test to determine whether the observed cell death occurred by apoptosis, cells were pretreated with IFNγ, then with a variety of cell death-inducing agents. DNA was isolated from adherent and non-adherent cells separately by proteinase K-phenol method as described. Sambrook et al. (1989). DNA samples were treated with 100 μg/ml of DNase-free RNase, extracted twice with phenol/chloroform, precipitated with ethanol and dissolved in 10 mM Tris-HCl, pH 7.6, 1 mM EDTA. DNA samples (10 μg) were fractionated by electrophoresis on 1.2% agarose gels and visualized by staining with ethidium bromide (0.5 Tg/ml). Sambrook, Fritsh, Maniatis (1989) In:*Molecular Cloning: A Laboratory Manual,* 2nd Ed., Cold Spring Harbor Laboratory, Cold Spring Harbor, N.Y.

Figure 12A:
FIGS. 12A–12B show agarose gel electrophoresis of DNA isolated from HT29 cells pretreated with IFN-γ, then treated with various cytotoxic agents.
Figure 12B:
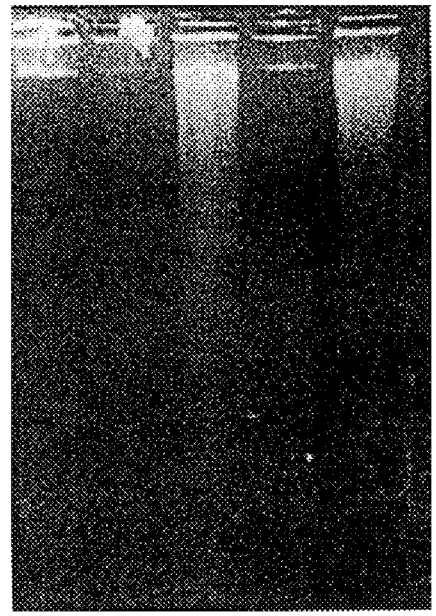

Cells pretreated with IFN-γ were incubated 16 hours without any additions (FIG. 12, lane 1) or in the presence of 100 ng/ml anti-Fas Ab (panel A, lanes 2 and 3), 1 μg/ml staurosporine (panel A, lanes 4 and 5), 20 μM C-2 ceramide (panel B, lanes 2 and 3) or C-6 ceramide (panel B, lanes 4 and 5). 30 mM KCN was added to induce necrotic cell death and DNA was isolated after 2 hours (panel A, lanes 6 and 7). Lanes 1, 2, 4 and 6 contain DNA from adherent cells; lanes 3, 5 and 7 contain DNA from non-adherent cells.

Agarose gel electrophoresis of DNA isolated from anti-Fas Ab-treated HT29 cells (panel A, lanes 2 and 3) showed nucleosomal laddering, indicating degradation of nuclear DNA characteristic of apoptotic cell death. Electron microscopy revealed typical apoptotic morphology of chromatin condensation without significant changes of cytoplasmic organelles (not shown). Taken together, these data suggest that IFN-γ sensitizes HT29 cells to apoptosis induced by crosslinking of TNFR 1 or CD95.

Apoptotic stimuli that act through different mechanisms also result in nucleosomal laddering pattern of DNA degradation. Staurosporine or ceramide treated cells showed nucleosomal DNA laddering (panel A, lanes 4 and 5; panel B, lanes 2–5), while treatment with KCN, a cytotoxic agent known to induce necrosis, did not produce such laddering (panel A, lanes 6 and 7).

Figure 13:
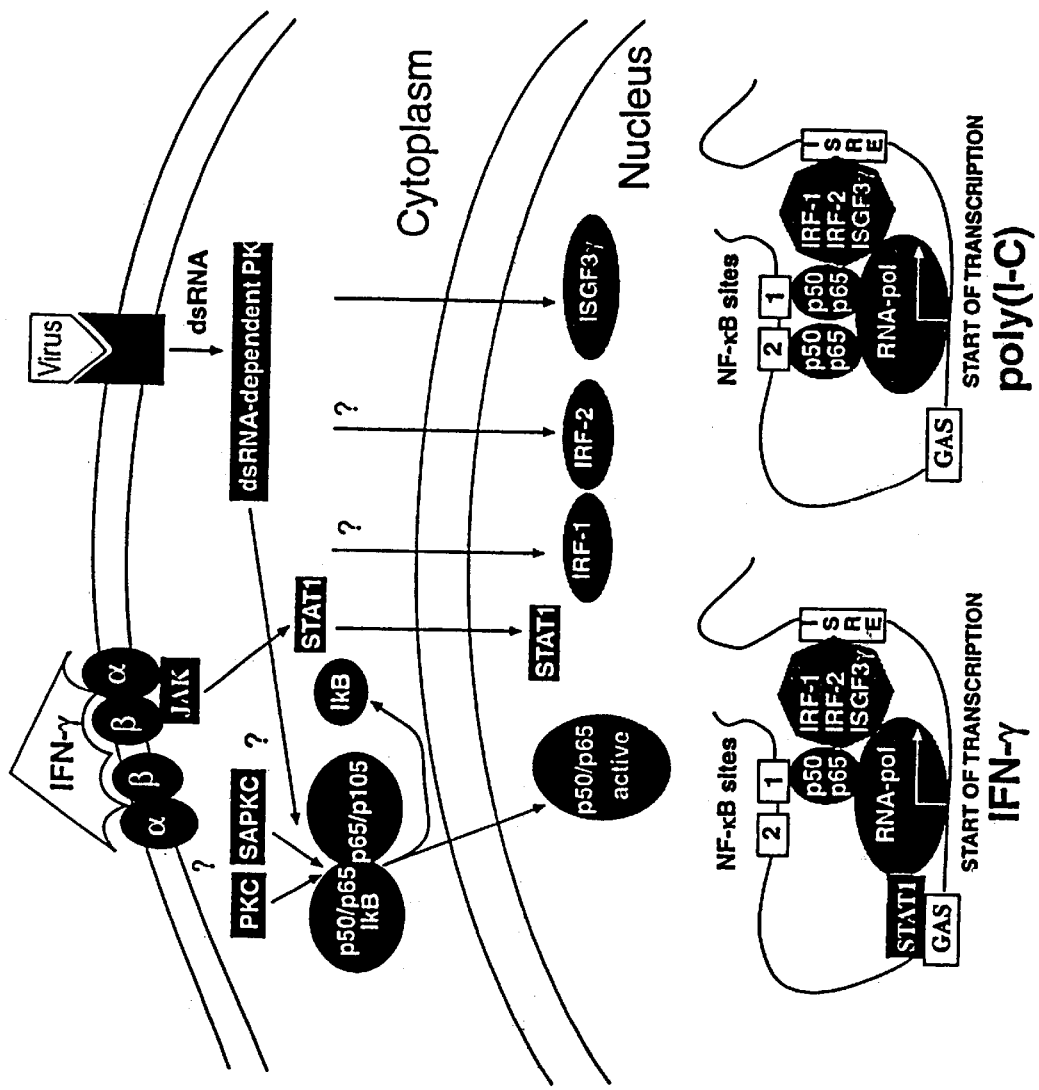
FIG. 13 shows a model for bak transcriptional activation by IFN-γ and virus (poly(I-C)).

Thus, IFN-γ sensitizes HT29 cells to pro-apoptotic but not pro-necrotic stimuli. This indicates that apoptotic pathways are being modulated by IFN-γ and suggests the mode of action involves the regulation of apoptosis-related proteins such as Bak (see FIG. 13).

EXAMPLE 9

Drug Screening Assay

This example describes an assay useful for screening for agents such as drugs that modulate the expression of the bak gene.

Figure 14:
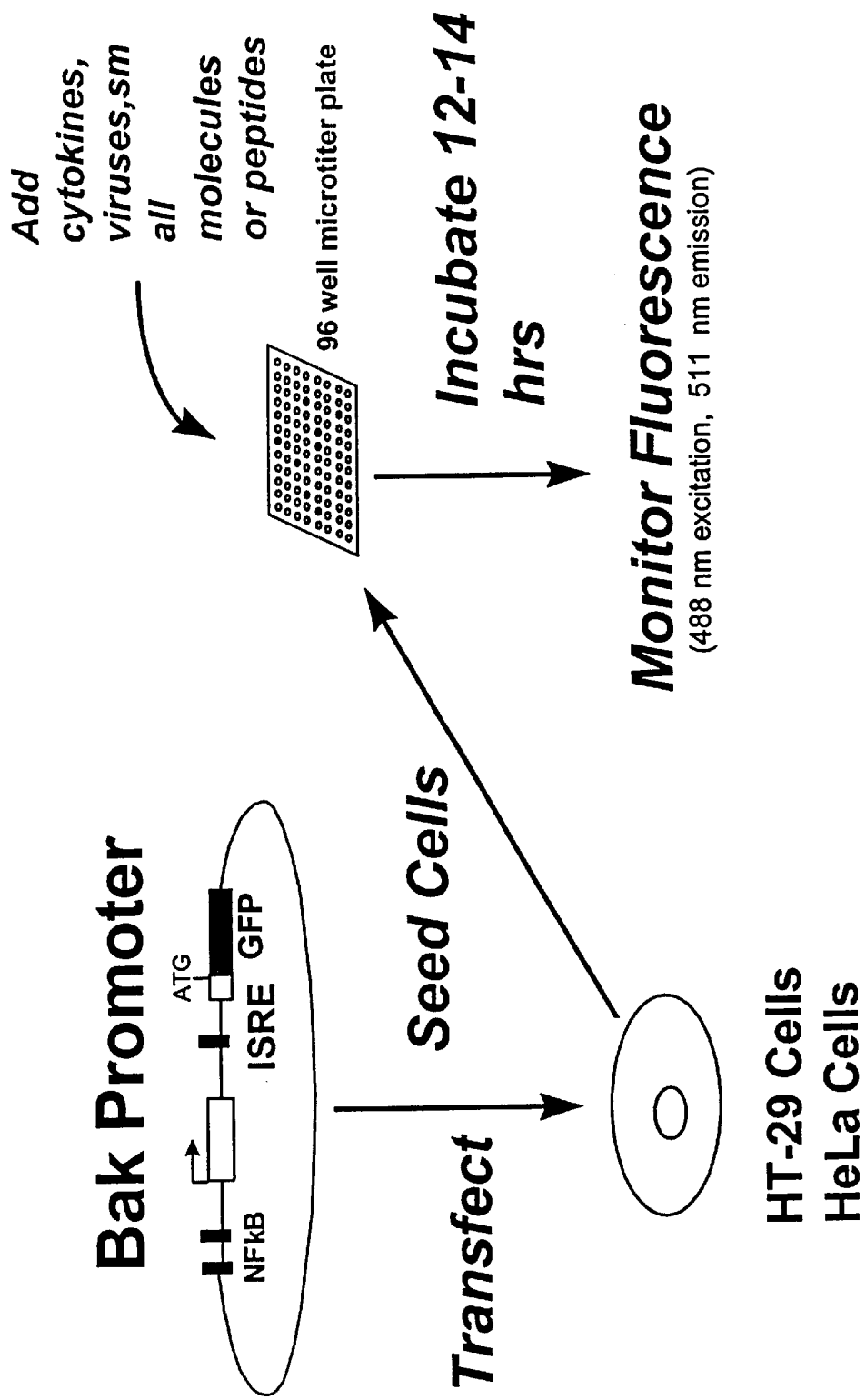
FIG. 14 shows a bak transcriptional screening assay to identify agents that modulate bak mRNA expression.

FIG. 14 presents a scheme for using the bak promoter in a drug screening assay that is suitable for automated high through-put random drug screening. A DNA sequence containing the bak promoter, including intron1, is linked to a DNA sequence encoding a second moiety that can serve as a detectable tag, e.g. green fluorescent protein (GFP; Prasher (1995) *Trends Genet.* 1 1:320–323), is stably transfected into a suitable cell line such as HT29 or HeLa cells. Cells are plated into a 96-well microtiter plate. After a suitable time, the agent whose ability to affect bak expression is to be tested is added. Control samples include no test agent. After a suitable incubation period, the test wells are washed, and fluorescence is monitored by measuring excitation at 488 nm and emission at 511 nm. Test wells showing a significantly higher or significantly lower fluorescence compared with the control are then examined further to confirm an effect on bak expression.

EXAMPLE 10

The bak gene promoter region contains 3 motifs with homology to consensus p53-binding sites. P53 is known as a direct transcriptional activator of the bax gene (U.S. Pat. No. 5,659,024, and Miyashita, T. and Reed, J.(1995) *Cell* 80:293–299). To explore the functional significance of the Bak potential p53-binding sites, a comparative EMSA for both Bak and Bax p53 sites was performed. For these experiments, wild-type p53 protein was produced in Sf9 cells using recombinant baculoviruses, and extracts from these cells were incubated with 32 P-labeled DNA probes containing either Bax or Bak p53 binding site motifs. The sequence of Bak p53 oligonucleotides is as follows:

5'-GAT CCA AAG TGG GCG GGA CAT GCT CCT
GGG CCT GGC CCA CCC AGA TCA CCC CTG-3'
(Sequence I.D. No: 11), and 5'-GAT CCA GGG GTG ATC TGG GTG GGC CAG
GCC CAG GAG CAT GTC CCG CCC ACT TTG-3'.
(Sequence I.D. No: 12).

Figures 15A, 15B:
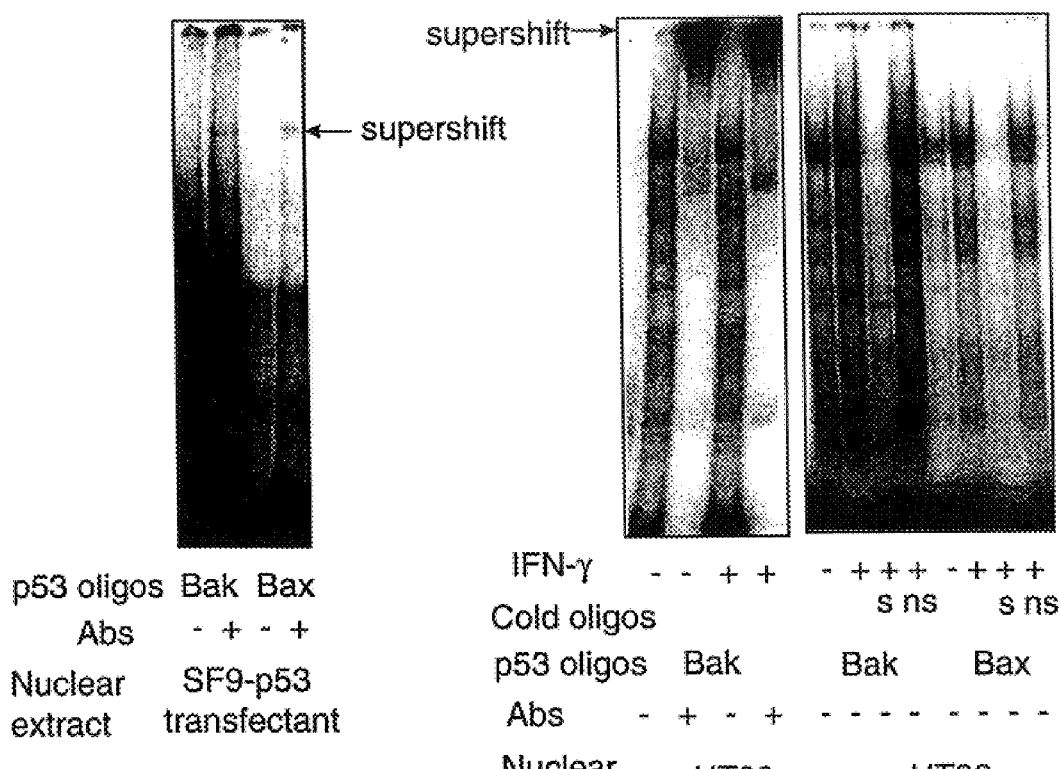
FIGS. 15A and 15B are photographs of electrophoretical mobility shift assays showing the binding of wild type p53 protein to Bak and Bax promoter p53 sites (FIG. 15A).

The Bax p53 sequence is described in U.S. Pat. No. 5,659,024. (See also Miyashita, T. and Reed, J.(1995) *Cell* 80:293–299). Antibodies directed against p53 were also included in some samples to help stabilize the in vitro interaction of p53 with target DNAs. (Miyashita, T. and Reed, J. (1995) *Cell* 80:293–299). As shown in FIG. 15A, both Bak and Bax p53 sites bound wild type p53 protein in the presence of antibodies. CAT assay also shows that wild type p53 can modulate Bak promoter activity (data not shown).

HT29 cells contain a non-functional p53 mutant protein. When the nuclear extracts from HT29 cells were incubated with p53 probe from Bak and Bax promoters, a number of complexes with shifted gel mobility were detected (FIG. 15B). Specificity of these complexes was confirmed by showing that a 50-fold molar excess of unlabeled homologous DNA (specific competitors) competed with the labeled p53 probe. These complexes were shifted up by preincubation with antibodies against p53 (Santa Cruz), suggesting the presence of p53 protein in all complexes. However, the binding activity of nuclear extracts to the bak p53 site was not effected by IFN-γ treatment (FIG. 15B).

EXAMPLE 11

Regulation of Bak Expression by ISRE "Decoy" Cis-Element

Synthetic double stranded oligonucleotides as "decoy" cis-elements block the binding of nuclear factors to promoter regions of targeted genes, resulting in the inhibition of gene transactivation. (Belinska, A. et al. (1990) *Cell* 250:997–1000). Double-stranded oligonucleotides corresponding to the Bak promoter cis-elements ISRE, GAS and κB1 (sequences are described in Example 6, herein) were used as "decoy" elements to regulate Bak expression. Scr (scrambled) DNA with random sequence was designed as a control oligonucleotide. The sequence of scrambled DNA was as follows:

5'-TTG CCG TAC CTG ACT TAG CC-3' (Sequence I.D. No: 13) and

3'-AAC GGC ATG GAC TGA ATC GG-5' (Sequence I.D. No: 14).

HT29 cells were incubated in Optimem media with 60 mM decoy DNA for 8 hours before IFN-γ treatment. IFN-γ was then added (200 U/ml) in McCoy's 5a media supplemented with 10% fetal bovine serum and the cells were incubated for an additional 16 hours. Total RNA was isolated by a single step extraction method (Chomczynski and Sacchi (1987) *Anal. Biochem.* 162:156–159) and used for Northern blot hybridization.

Figure 16:
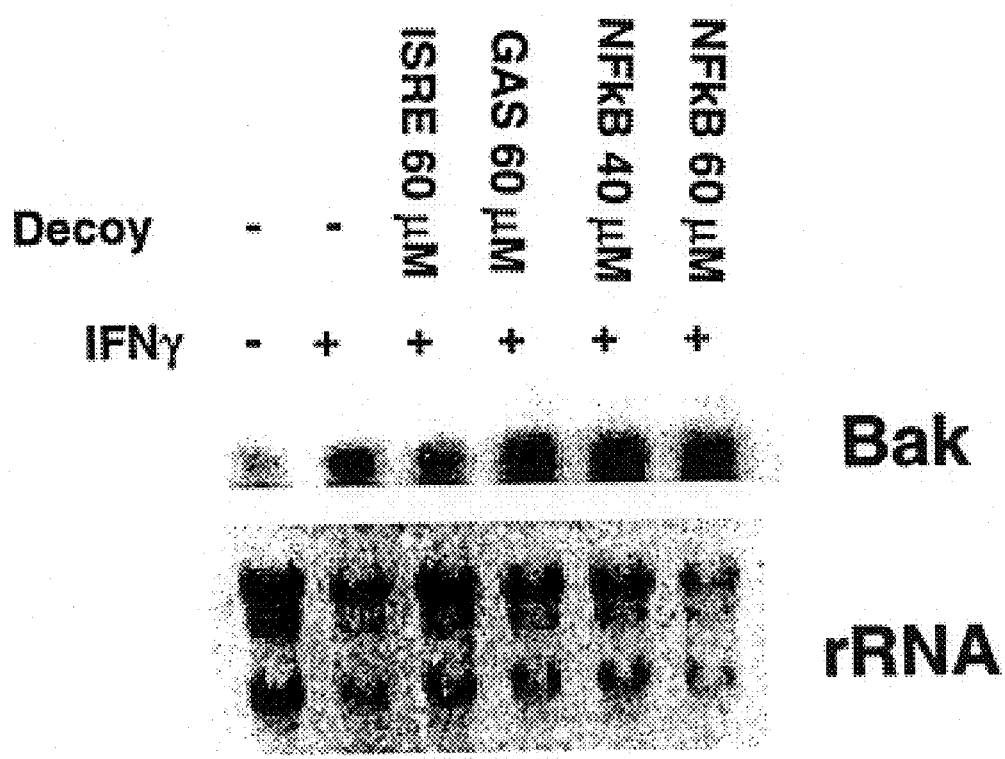
FIG. 16 is a photograph of a northern blot analysis showing the effect of treatment with ISRE, GAS and κB1 "decoy" DNA, as well as control "scrambled" DNA, on Bak expression in response to IFN-γ in HT29 cells.

Bak mRNA expression following IFN-γ treatment in the presence of "decoy" DNA was analyzed. FIG. 16 shows that treatment by ISRE "decoy" DNA, but not scrambled decoy, markedly inhibited Bak expression in response to IFN-γ in HT29 cells. In contrast the GAS and κB1 "decoy" DNAs failed to inhibit Bak expression. Thus, these studies confirm the CAT assay data that the ISRE cis-element is critical for Bak gene activation. Moreover, ISRE decoy DNA can be used as a tool for inhibition of Bak transcription.

Although the foregoing invention has been described in some detail by way of illustration and example for purposes of clarity and understanding, it will be apparent to those skilled in the art that certain changes and modifications may be practiced. Therefore, the description and examples should not be construed as limiting the scope of the invention, which is delineated by the appended claims.

We claim:

1. An isolated polynucleotide of about 4066 or fewer nucleotides selected from the group consisting of:
   (a) an isolated polynucleotide comprising the bak promoter (positions 1–4021 of SEQ ID NO:1);
   (b) an isolated polynucleotide comprising a fragment of said bak promoter of (a) that has at least basal bak promoter transcriptional activity;
   (c) an isolated mutated polynucleotide of (a) or (b) comprising a mutation selected from the group consisting of a point mutation and a deletion, said mutated polynucleotide having at least basal bak promoter transcriptional activity; and
   (d) an isolated polynucleotide comprising a nucleic acid sequence that is fully complementary to said polynucleotide of (a), (b) or (c).

2. The polynucleotide of claim 1, wherein said fragment comprises an ISRE site of said bak promoter (positions 2945–2967 of SEQ ID NO:1).

3. The polynucleotide of claim 1, wherein said fragment comprises an SP1 site and a GAS site of said bak promoter (positions 1646–1662 of SEQ ID NO:1).

4. The polynucleotide of claim 1, wherein said fragment comprises an NFκB2 site of said bak promoter (positions 1038–1047 of SEQ ID NO:1).

5. The polynucleotide of claim 1, wherein said fragment comprises an NFκB1 site of said bak promoter (positions 949–958 of SEQ ID NO:1).

6. The polynucleotide of claim 1, wherein said fragment comprises a p53 cluster and an SP1 site of said bak promoter (positions 1431–1473 of SEQ ID NO:1).

7. A method for identifying an agent that regulates bak promoter activity, comprising the steps of:
   a) introducing into a cell a recombinant polynucleotide comprising a reporter gene operably linked to a bak promoter polynucleotide, wherein said bak promoter polynucleotide is selected from the group consisting of:
      (i) a polynucleotide comprising a bak promoter (positions 1–4021 of SEQ ID NO:1);
      (ii) a polynucleotide comprising a fragment of said bak promoter of (i) that has at least basal bak promoter transcriptional activity; and
      (iii) a mutated polynucleotide of (i) or (ii) comprising a mutation selected from the group consisting of a point mutation and a deletion, said mutated polynucleotide having at least basal bak promoter transcriptional activity;
   b) determining the level of expression of said reporter gene in said cell of step (a) in the absence of a test agent;
   c) contacting said cell of step (a) with said test agent;
   d) determining the level of expression of said reporter gene in said cell after step (c) of contacting; and,
   e) identifying an agent that regulates the expression of said reporter gene determined in step (d), as compared to the level of expression determined in step (b), wherein a difference in the expression of said reporter gene in step (d) as compared to step (b) indicates that the agent regulates bak promoter activity.

8. A method for identifying an agent that increases the expression of a gene that is operably linked to a bak promoter, comprising the steps of:
   a) introducing into a cell a recombinant polynucleotide comprising a reporter gene operably linked to a bak promoter polynucleotide wherein said bak promoter polynucleotide is selected from the group consisting of:
      (i) a polynucleotide comprising a bak promoter (positions 1–4021 of SEQ ID NO:1);
      (ii) a polynucleotide comprising a fragment of said bak promoter of (i) that has at least basal bak promoter transcriptional activity; and
      (iii) a mutated polynucleotide of (i) or (ii) comprising a mutation selected from the group consisting of a point mutation and a deletion, said mutated polynucleotide having at least basal bak promoter transcriptional activity;
   b) determining the level of expression of said reporter gene in said cell of step (a) in the absence of a test agent;
   c) contacting said cell of step (a) with said test agent;
   d) determining the level of expression of said reporter gene in said cell after step (c) of contacting; and,
   e) identifying an agent that increases the expression of said reporter gene determined in step (d), as compared to the level of expression determined in step (b), wherein an increase in the expression of said reporter gene in step (d) as compared to step (b) indicates that the agent increases expression of a gene that is operably linked to a bak promoter.

9. A method for identifying an agent that decreases the expression of a gene that is operably linked to a bak promoter, comprising the steps of:
   a) introducing into a cell a recombinant polynucleotide comprising a reporter gene operably linked to a bak promoter polynucleotide, wherein said bak promoter polynucleotide is selected from the group consisting of:
      (i) a polynucleotide comprising a bak promoter (positions 1–4021 of SEQ ID NO:1);
      (ii) a polynucleotide comprising a fragment of said bak promoter of (i) that has at least basal bak promoter transcriptional activity; and
      (iii) a mutated polynucleotide of (i) or (ii) comprising a mutation selected from the group consisting of a point mutation and a deletion said mutated polynucleotide having at least basal bak promoter transcriptional activity;
   b) determining the level of expression of said reporter gene in said cell of step (a) in the absence of a test agent;
   c) contacting said cell of step (a) with said test agent;
   d) determining the level of expression of said reporter gene in said cell after step (c) of contacting; and,
   e) identifying an agent that decreases the expression of said reporter gene determined in step (d), as compared to the level of expression determined in step (b), wherein a decrease in the expression of said reporter gene in step (d) as compared to step (b) indicates that the agent decreases expression of a gene that is operably linked to a bak promoter.

10. The isolated polynucleotide of claim 1, wherein said fragment is an about 0.7 kb fragment comprising from at least about the first nucleotide of an NFκB1 site (position 949 of SEQ ID NO:1) through at least about the first transcription start site in said bak promoter (position 1515 of SEQ ID NO:1).

11. The isolated polynucleotide of claim 1, wherein said fragment is an about 1.6 kb fragment comprising from at least about the first nucleotide of said bak promoter (position 1 of SEQ ID NO:1) through at least about the first transcription start site that is 3' of GAS (position 1695 of SEQ ID NO:1).

12. The isolated polynucleotide of claim 1, wherein said fragment is an about 2 kb fragment comprising from at least about the first nucleotide that is 3' of an NFκB2 site (position 1048 of SEQ ID NO:1) through at least about the last nucleotide of an ISRE in intron 1 of said bak promoter (position 2967 of SEQ ID NO:1).

13. The isolated polynucleotide of claim 1, wherein said fragment has interferon-γ (IFN-γ)-activated bak promoter activity.

14. A recombinant polynucleotide, comprising an isolated polynucleotide having at least basal bak promoter transcriptional activity, operably linked to a coding sequence, wherein said isolated polynucleotide is selected from the group consisting of:
   (a) an isolated polynucleotide comprising the bak promoter (positions 1–4021 of SEQ ID NO:1);
   (b) an isolated polynucleotide comprising a fragment of said bak promoter that has at least basal bak promoter transcriptional activity; and
   (c) a mutated polynucleotide of (a) or (b) comprising a mutation selected from the group consisting of a point mutation and a deletion, said mutated polynucleotide having at least basal bak promoter transcriptional activity.

15. The recombinant polynucleotide of claim 14, wherein said coding sequence is a heterologous polynucleotide with respect to said isolated polynucleotide.

16. A recombinant cell transfected with a recombinant polynucleotide of claim 14.

17. The method of claim 7, wherein said fragment is an about 0.7 kb fragment comprising from at least about the first nucleotide of an NFκB1 site (position 949 of SEQ ID NO:1) through at least about the first transcription start site in said bak promoter (position 1515 of SEQ ID NO:1).

18. The method of claim 7, wherein said fragment is an about 1.6 kb fragment comprising from at least about the first nucleotide of said bak promoter (position 1 of SEQ ID NO:1) through at least about the first transcription start site that is 3' of GAS (position 1695 of SEQ ID NO:1).

19. The method of claim 7, wherein said fragment is an about 2 kb fragment comprising from at least about the first nucleotide that is 3' of an NFκB2 site (position 1048 of SEQ ID NO:1) through at least about the last nucleotide of an ISRE in intron 1 of said bak promoter (position 2967 of SEQ ID NO:1).

20. An isolated polynucleotide selected from the group consisting of:
 (a) an isolated polynucleotide consisting essentially of the bak promoter (positions 1–4021 of SEQ ID NO:1);
 (b) an isolated polynucleotide comprising a fragment of said bak promoter of (a) that has at least basal bak promoter transcriptional activity;
 (c) an isolated mutated polynucleotide of (a) or (b) comprising a mutation selected from the group consisting of a point mutation and a deletion, said mutated polynucleotide having at least basal bak promoter transcriptional activity; and
 (d) an isolated polynucleotide consisting essentially of a nucleic acid sequence that is fully complementary to said polynucleotide of (a), (b) or (c).

* * * * *

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
      (A) LENGTH: 4066 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: 4022..4066

(ix) FEATURE:
      (A) NAME/KEY: mat_peptide
      (B) LOCATION: 4022

(xi) SEQUENCE DESCRIPTION: SEQ ID NO:1:

```
GATCTGCCTG CCTCGGGCTC CCAAAGTGCT GGGATGGGAT TACAGGCGTG AGCCACCGTG      60

CCCGGCCTTT TTTTTTTTTT TTTTTTTTTT TCTAGAGACA GACTCTCCCT CTGTTGCCCT     120

GGTGCAATCA TAGCTTACTG CAGCCTCGAC CTCCTGGACT CAAGCAATCC TCCCACCTCA     180

GCCTCCCCAG TAGCTAAGAC CACAGGCATA CAACACCATG CCTTGCTAAT TTTTTTTTTT     240

TTTTTTTTTT TTTTGGTAT AAGCAGGGTA TTGCTGTTGC CCAGGCTGGC CTGGAACTCC      300
```

-continued

```
TGCACCTGGC CTCAAGCGAT CCTCTTGCCT TGGCCTCCCA AATGGCTGGG ATGGGATTCT      360

AGGCGTGACA CACCGCAGCT GGCTGCCTTT TTTGTTGTTG TTGAGACAAG GTCTTGCTCT      420

GTTGCCCAGG GCGGAATGCA GTGGTGCAAA CATGGCTCAC TGCGGCCTCG ACTTCCTGTG      480

CTCAGGTGAT CCTCCTGCCT CAGCCTCCTA GGTAGCTGGG ACCACCAAAT GCACAGGTGT      540

GCACTACCAT ACCCAGCTAA TTTCTAATTT TTTTTTGTAG AGACATGGTC TCACTTTGTT      600

GCCCAGGCTG GTCTTGAACT CCTGGGCTCA AGCAATCCTC CCACCTCAGC CTTCCAAAGT      660

GTTGGGATTA CAGGCGTGAG CCACTGGGCC CAGCCTCTAT TGAGTTTTAA TCTCCGTTTA      720

CTTGACTATC ACCTTCAGGA TTTCAAACAT CCAGAGACCA CCAAGGTGCA TGGTGCACAG      780

GTCTAAATTG CAGGTTGAAT CTCAATCTAG TATTAGTATT CCCCAATGCG ACTACAGAAC      840

TGATTATTAC TATTTATTTT TTTTTGAGAT GGAGTCTTGC ACTGTCACCA GGCTGGAGT      900

GCAATGGCGC AATCCTGGTT TACTGCAACC TCCACCTCCC AGGTTCAAGG GATTCTCCTG      960

CCTCAGCCTT CCAACTAGCT GGGATTACAG GCGCCCGCCA CCACACCCAG CTAATTTTTT     1020

GTATTTTTAG TAGAGACGGG GTTTCACCAT GTTAGCCAGA ATGGTCTCGA TCTCTTGACC     1080

TCGTGATCTG CCTGCCTCAG CCTCCCAAGG TGCTGGGATT ATAGGCGTGA GCCACCGCGC     1140

CTGGCCCAGA ACTGATGATT AACCCAGATG AGCCTCTGTT CATCTGAATG GGTATTGTCA     1200

ACAGCACTCA CTTACAAGAG TTGCTGAGAA GATCCAATGA GACAAATAGT TGCTAAAGTG     1260

CCAGGCATGC AGCAGTGCTT AAGAAACTTC TCACCCTGGG TTTTTTATTG GTATTGATTG     1320

ATGTAGAGGT GGGGGAGAAG ATCAAAGACA AGGATTGAGA ATCAGGGATG GGAAAAGCAG     1380

TGGGCCACTG ACAGCCGCCC TGCCTGCCTG GGAGGTGGGG TGGGGAAAGT GGGCGGGACA     1440

TGCTCCTGGG CCTGGCCCAC CCAGATCACC CCTACAGGCT GTCGGCCTGT GCGTCTGCAT     1500

CCGGTGGCCA CAGAGCAACT TCCTCTAGAG GGAGCTGATT GGAGCCGGGT GCCGCTGGCA     1560

CCTCTATGAT CACTGGAGTC TCGCGGGTCC CTCGGGCTGC ACAGGACAA GTAAAGGCTA     1620

CATCCAGATG CCGGGAATGC ACTGACGCCC ATTCCTGGAA ACTGGGCTCC CACTCAGCCC     1680

CTGGGAGCAG CAGCCGCCAG CCCCTCGGGA CCTCCATCTC CACCCTGCTG AGCCACCCGG     1740

GTTGGGCCAG GATCCCGGCA GGTAAGCTGG AAGGGTCTTG TCCATCCTCC CAGATCTCAG     1800

CAGCCCCAGC CCCAGGGTGG GGCAGGGAGC CTGCCGGGAG CCGGGTGGGG AAGGGGAAGC     1860

TCAAGGCTTC CCTGGGCAGG TCTGCCGCCC CGGCTGGGGA CCTGATCCTG CCATGCCTGC     1920

CTCTGGCTGC CCCTCACAGC TTCCCCTCTT GGCCCAGCCC TGGATGCCGG AGAACTGTAA     1980

GAACTGGGTC CTTTAACAGT CTGGGAGATG GGAGTGGAGG TCAGAGCCAA GGTCAAGGGC     2040

AGAGAGAGAA CTTTCTCAGC GCTTGCTGCT GCCCAACATC CCTAGACTGG GTCCAGGGCC     2100

TGGCCAGGCA TGTATCCCTG GGAACATTC ATCGGGCCC AGCAAGCCCA GGAAGTCGGG     2160

GGTGGCTCCC CTCACCGGGA ATTTAGGCCA CTTGGATGGG GGAGGCAGAG CTAGGCCTGA     2220

GTCAGCATAG GTTGCTGGCC TTGGTGGGTG TTCTGAGGCT CTACCTGCTC CCCTCGGAAG     2280

CCTGGGGTGT TGGTAGAGGG AGTTGGAGGT GCAGTCAGCA TCCTCCAGCC CTACTGTCCT     2340

GGGGGTGCCG GGTCCTGGAG ACTGGGGAAG AAGGAAGGCC ATCTTATGTA AGGAGCTACG     2400

GGGGGTGGGA GGCAAGCAAA ACTCTTTTTT TTTGTTTTTT GAAATGGAGT CTCGCTCTGT     2460

TGCCCAGGCT GGAGTGCAGT GGCGCAATCT CGGCTGACCG CAACCTCCGC CTCCAAGGTT     2520

CAAGCGATTC TCCTGCCTCA GCCTCCCGAG TAGCTGGGAC TACAGGCGCA CGCACCATGC     2580

CCAGCTAATT TTTGTATTTT TAGTAGAGAT GGGGTTTCAT TATGTTGGCC AGGCTGGTCT     2640
```

```
TGAACTTCTG ACCTCGTGGG CCACTATGCC CGGCTGCAAA GTTCTGTTTT AACAAGGCCT    2700

TGCCCCTAGA GGTGGAGGAG AGGAGGGTCT GCCTTCGCCC TGTCCCTGTC CGGCAGATCG    2760

AGGAGGAGTG GGGAGCTGGG TGAGGGCACA GGTGGTCCAG GTCCCCAGGC CCTGGGCGGT    2820

GGGGGTGGGG CTGTGTGCTT GGCCCAGGGT GGGGCTGCAC ACCCCCTCCC TCTGGGATAG    2880

GAGGAGGGCG CTCTCCTTCT GAGGGCTGGA GGCTGCCTGG GGAAATGGGG CTCTGGGAGG    2940

GGTGCAAACT GAAAGTGAAA CAGCTGACAT CCAGGAAACA CTCACCCTGA TGAGGGGTCA    3000

CAGCAGGTTG GGGCTGCGGT CAGGACCAGG CAAAGAGGAA AATTGGGGCC GGGGACAGAA    3060

GACCAGGTGT GTGGTGGGAG TACGAGGCAG GTTATGGGGC TTCAAAGAAG GCCCTGATCC    3120

AGAACACACT CTGAGGTCCA CAAACTGGAA AAGAAATCTT GCATGCGTGT TGAGTACATG    3180

GACTCACGGA GATTCAGACA AACAACCTGA CTTTCCGTGA CTAACGATGT GACCTCGGGG    3240

CACTCAACTC TTTGTGCCTC ACTTTTCCTG CCTGTAAAGT GGGTATGATG GCGCTCACCC    3300

TGCTGGGTTC ATGTGAGTTT CCAGTGTTCA CCACCCACAG AGTGCTCCTA AGTGGGAGAG    3360

TATATCTTAG GCTCTCAGGA AATGTTTGCG GCTAACAGCC CAGAGTTAAA AAACAGGTGT    3420

GTTCTGGCCA GCCAGAGGGA AGTAGGGCCT CTGAGGACAG CCTTCATGGG CCATTGGCTG    3480

GGCAGTGGCT CGCTTGCAAT AAGCATGTGC TGGGTGGGCT GCAGGAGGCC CCAGGAACAG    3540

CTAAAAACCC CCCAGGCTCT TGCCCCAGGA GTGGCATGAA CTTGAGAGCC AGCGGGCACT    3600

GCTGCAGCCA CACCCTCCTC GATGGTGCAG ATACCTCAGT CTGCCCTTGG CTGCCTCACC    3660

TTCTTACCCT GTCTCCCTCA AGAGGGAGT GTTCAGTAAG TTGTTTCCTC CCAGCAGACT    3720

TCACTGGGAC CCATGCTGGA GTAAGAATAA AAAGTCCCAG AGGAGGCCAG GCACGGTGGC    3780

TCACACCTGT AATCCCAGCA CTGTGGATGG CCGAGGCAGA CTCACGAGGT CAGGAGTTTG    3840

AGACCGGCCT GGCCAAAGTC CCAGAGGACT AAGGGCCTTT CTGGGAATGG GGATCCTCT    3900

CTCCTATGTG GACATGGCAA CCTGTATGGG GTCCCCAGTC ACAGGTCTGT GCTCACCCCC    3960

ATCTCTGCTT TTTCTCGCCC TTCCCCGCAG GCTGATCCCG TCCTCCACTG AGACCTGAAA    4020

A ATG GCT TCG GGG CAA GGC CCA GGT CCT CCC AGG CAG GAG TGC GGA       4066
  Met Ala Ser Gly Gln Gly Pro Gly Pro Pro Arg Gln Glu Cys Gly
    1               5                  10                  15
```

(2) INFORMATION FOR SEQ ID NO:2:

(i) SEQUENCE CHARACTERISTICS:
        (A) LENGTH: 15 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ala Ser Gly Gln Gly Pro Gly Pro Pro Arg Gln Glu Cys Gly
  1               5                  10                  15
```

(2) INFORMATION FOR SEQ ID NO:3:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:3:

```
GCAAACTGAA AGTGAAACAG CT                                              22
```

(2) INFORMATION FOR SEQ ID NO:4:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:4:

CAGGTTCAAG GGATTCTCCT GCCTCA    26

(2) INFORMATION FOR SEQ ID NO:5:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:5:

AGATCTGAAT TCCTGTTTGA GAGTGGCATC AATTGG    36

(2) INFORMATION FOR SEQ ID NO:6:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:6:

AGATCTGCGG CCGCAGTCAT GATTTGAAGA ATCTTCGTAC    40

(2) INFORMATION FOR SEQ ID NO:7:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:7:

AGATCTGAAT TCGTGAGTAT CCAAGGACTG CAA    33

(2) INFORMATION FOR SEQ ID NO:8:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:8:

AGATCTAAGC TTCTGCCGGG AGAAACAAGG TG    32

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:9:

CGCCCATTCC TGGAAACTGG    20

(2) INFORMATION FOR SEQ ID NO:10:

(i) SEQUENCE CHARACTERISTICS:
    (A) LENGTH: 26 base pairs
    (B) TYPE: nucleic acid
    (C) STRANDEDNESS: single
    (D) TOPOLOGY: linear (xi) SEQUENCE DESCRIPTION: SEQ ID NO:10:

AGTAGAGACG GGGTTTCACC ATGTTA                                26

(2) INFORMATION FOR SEQ ID NO:11:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO:11:

GATCCAAAGT GGGCGGGACA TGCTCCTGGG CCTGGCCCAC CCAGATCACC CCTG     54

(2) INFORMATION FOR SEQ ID NO:12:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO:12:

GATCCAGGGG TGATCTGGGT GGGCCAGGCC CAGGAGCATG TCCCGCCCAC TTTG      54

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:13:

TTGCCGTACC TGACTTAGCC                                           20

(2) INFORMATION FOR SEQ ID NO:14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:14:

GGCTAAGTCA GGTACGGCAA                                           20